(12) United States Patent
Rohrer et al.

(10) Patent No.: US 11,915,361 B2
(45) Date of Patent: Feb. 27, 2024

(54) SYSTEM, METHOD, AND COMPUTER PROGRAM PRODUCT FOR PREDICTING, ANTICIPATING, AND/OR ASSESSING TISSUE CHARACTERISTICS

(71) Applicant: BAYER AKTIENGESELLSCHAFT, Leverkusen (DE)

(72) Inventors: Martin Rohrer, Berlin (DE); Gesine Knobloch, Berlin (DE); Arthur Uber, III, Pittsburgh, PA (US)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 17/753,564

(22) PCT Filed: Sep. 17, 2020

(86) PCT No.: PCT/IB2020/058688
§ 371 (c)(1),
(2) Date: Mar. 8, 2022

(87) PCT Pub. No.: WO2021/053585
PCT Pub. Date: Mar. 25, 2021

(65) Prior Publication Data
US 2022/0414972 A1    Dec. 29, 2022

Related U.S. Application Data

(60) Provisional application No. 62/943,969, filed on Dec. 5, 2019.

(30) Foreign Application Priority Data

Sep. 18, 2019   (EP) ..................................... 19197989

(51) Int. Cl.
*G06K 9/00*     (2022.01)
*G06T 15/08*    (2011.01)
(Continued)

(52) U.S. Cl.
CPC ............ *G06T 15/08* (2013.01); *G06T 7/0016* (2013.01); *G06V 10/62* (2022.01); *G06T 2207/30024* (2013.01)

(58) Field of Classification Search
CPC ....... A61B 5/055; A61B 5/0263; A61B 6/481; A61B 8/481; G06T 2207/10088–10096;
(Continued)

(56) References Cited

U.S. PATENT DOCUMENTS 732,697 A    7/1903  Bates
5,732,697 A  3/1998  Zhang et al.
(Continued)

FOREIGN PATENT DOCUMENTS

CN    104769641 A    7/2015
CN    107492090 A    12/2017
(Continued)

OTHER PUBLICATIONS

Bellani; Giacomo et al, "Epidemiology, Patterns of Care, and Mortality for Patients With Acute Respiratory Distress Syndrome in Intensive Care Unites in 50 Countries", JAMA, 2016.
(Continued)

*Primary Examiner* — Atiba O Fitzpatrick
(74) *Attorney, Agent, or Firm* — David Schramm; James R. Stevenson; Joseph L. Kent

(57) ABSTRACT

A system, method, and computer program product for predicting, anticipating, and/or assessing tissue characteristics obtains measurement information associated with a parameter of a voxel of tissue of a patient measured at two or more time points, the two or more time points occurring before one or more characteristics of the voxel of the tissue are separable in an image generated based on the parameter of the voxel measured at a single time point of the two or more time points, and determines, based on the parameter of the (Continued)

voxel at the two or more time points, the one or more characteristics of the voxel of the tissue.

23 Claims, 10 Drawing Sheets

(51) Int. Cl.
  *G06V 10/62* (2022.01)
  *G06T 7/00* (2017.01)
(58) Field of Classification Search
  CPC ........... G06T 11/00; G06T 2200/00–08; G06T 2210/00; G06T 2210/41; G06T 2211/00; G06T 2207/30056; G06T 2207/30101; G06T 2207/20081; G06T 2207/20084; G06T 7/0012–0016; G06T 2207/10064–10136; G06T 2207/30004–30104; G01R 33/5608; G01R 33/5635; G01R 33/5601; G01R 33/56325; A61K 49/06; G16H 50/50; G16H 50/70; G06V 10/778–7792; G06V 2201/031; G06V 10/70; G06V 10/82; G06V 10/774–7796; G06V 10/62; G06V 2201/03–034; G06N 3/084; G06N 3/02–126; G06N 20/00–20; G06N 5/046; G06N 5/04; G06N 7/00; G06K 9/6263; G06K 9/6256; G06K 9/6257; G06K 9/6259
  See application file for complete search history.

(56) References Cited

U.S. PATENT DOCUMENTS

| | | | |
|---|---|---|---|
| 5,840,026 A | 11/1998 | Uber, III et al. | |
| 6,039,931 A | 3/2000 | Schmitt-Willich et al. | |
| 6,643,537 B1 | 11/2003 | Zatezalo et al. | |
| 6,754,376 B1 | 6/2004 | Turek et al. | |
| 6,819,790 B2 | 11/2004 | Suzuki et al. | |
| 7,564,990 B2 | 7/2009 | Kern et al. | |
| 7,738,683 B2 | 6/2010 | Cahill et al. | |
| 7,937,134 B2 | 5/2011 | Uber et al. | |
| 7,949,167 B2 | 5/2011 | Krishnan et al. | |
| 8,060,178 B2 | 11/2011 | Zhou et al. | |
| 8,155,406 B2 | 4/2012 | Mattiuzzi | |
| 9,311,702 B2 | 4/2016 | Pautot | |
| 9,449,381 B2 | 9/2016 | Liang | |
| 9,616,166 B2 | 4/2017 | Kalafut et al. | |
| 9,754,371 B2 | 9/2017 | Kateb et al. | |
| 9,959,615 B2 | 5/2018 | Liang et al. | |
| 10,157,467 B2 | 12/2018 | Dincer et al. | |
| 10,176,408 B2 | 1/2019 | Paik et al. | |
| 10,335,106 B2 | 7/2019 | Kim | |
| 10,555,773 B2 | 2/2020 | Higaki et al. | |
| 10,645,359 B2 | 5/2020 | Bist et al. | |
| 10,933,186 B2 | 3/2021 | Uber, III | |
| 11,246,558 B2 | 2/2022 | Uber, III et al. | |
| 11,308,613 B2 | 4/2022 | Chitiboi et al. | |
| 2005/0100208 A1 | 5/2005 | Suzuki et al. | |
| 2006/0018524 A1 | 1/2006 | Suzuki et al. | |
| 2007/0047787 A1 | 3/2007 | Oakley et al. | |
| 2008/0317315 A1 | 12/2008 | Stemmer | |
| 2010/0198054 A1 | 8/2010 | Ewing et al. | |
| 2011/0029248 A1 | 2/2011 | Saeed et al. | |
| 2013/0035921 A1 | 2/2013 | Rodriguez-Ponce et al. | |
| 2013/0297554 A1 | 11/2013 | Mah | |
| 2014/0062481 A1 | 3/2014 | Greiser et al. | |
| 2014/0257854 A1 | 9/2014 | Becker et al. | |
| 2015/0125398 A1 | 5/2015 | Assouline et al. | |
| 2016/0000945 A1 | 1/2016 | Nedergaard et al. | |
| 2016/0035093 A1 | 2/2016 | Kateb et al. | |
| 2016/0038092 A1 | 2/2016 | Golay | |
| 2016/0109539 A1 | 4/2016 | Mardor et al. | |
| 2017/0243349 A1* | 8/2017 | Hou | G06V 10/40 |
| 2017/0245817 A1 | 8/2017 | Berlin et al. | |
| 2017/0269182 A1 | 9/2017 | Beck | |
| 2017/0281278 A1* | 10/2017 | Higaki | A61B 6/504 |
| 2018/0242917 A1* | 8/2018 | Bagherzadeh | A61B 5/7221 |
| 2018/0315183 A1* | 11/2018 | Milioni De Carvalho | G16H 20/10 |
| 2019/0012932 A1 | 1/2019 | Higaki et al. | |
| 2019/0099145 A1 | 4/2019 | Kim | |
| 2019/0122348 A1 | 4/2019 | Jensen | |
| 2019/0310338 A1 | 10/2019 | James et al. | |
| 2019/0317171 A1* | 10/2019 | Nayak | A61B 5/055 |
| 2019/0318474 A1 | 10/2019 | Han | |
| 2019/0362522 A1 | 11/2019 | Han | |
| 2019/0365340 A1* | 12/2019 | Hao | G06T 5/50 |
| 2020/0167911 A1 | 5/2020 | Park et al. | |
| 2020/0202557 A1 | 6/2020 | Schmidt | |
| 2020/0242744 A1* | 7/2020 | Schafer | G06F 18/2431 |
| 2020/0258629 A1 | 8/2020 | Ahmad et al. | |
| 2020/0311932 A1 | 10/2020 | Hooper et al. | |
| 2020/0371182 A1* | 11/2020 | Grimm | G01R 33/56366 |
| 2021/0012486 A1 | 1/2021 | Huang et al. | |
| 2021/0027436 A1 | 1/2021 | Banerjee et al. | |
| 2021/0027502 A1* | 1/2021 | Abumoussa | A61B 6/507 |
| 2021/0056734 A1 | 2/2021 | Han | |
| 2021/0386389 A1 | 12/2021 | Freiman et al. | |
| 2022/0018924 A1* | 1/2022 | Bai | G01R 33/56366 |
| 2022/0031270 A1* | 2/2022 | Cohen | A61B 5/065 |
| 2022/0105265 A1 | 4/2022 | Cowan et al. | |
| 2022/0351369 A1* | 11/2022 | Haase | A61B 6/504 |

FOREIGN PATENT DOCUMENTS

| | | |
|---|---|---|
| CN | 108324244 A | 7/2018 |
| CN | 109983474 A | 7/2019 |
| EP | 1941460 A1 | 7/2008 |
| EP | 2626718 A1 | 8/2013 |
| EP | 2750102 A1 | 7/2014 |
| EP | 3118644 A1 | 1/2017 |
| EP | 3322997 A1 | 5/2018 |
| EP | 3619631 A1 | 3/2020 |
| EP | 3804615 A1 | 4/2021 |
| EP | 3875979 A1 | 9/2021 |
| JP | 5878009 B2 | 3/2016 |
| KR | 102001398 B1 | 7/2019 |
| WO | 2007053676 A2 | 5/2007 |
| WO | 2009135923 A1 | 11/2009 |
| WO | 2012075577 A1 | 6/2012 |
| WO | 2013121374 A2 | 8/2013 |
| WO | 2014162273 A1 | 10/2014 |
| WO | 2016007734 A1 | 1/2016 |
| WO | 2017040152 A1 | 3/2017 |
| WO | 2017139110 A1 | 8/2017 |
| WO | 2018046412 A1 | 3/2018 |
| WO | 2018183044 A1 | 10/2018 |
| WO | 2018200493 A1 | 11/2018 |
| WO | 2018202541 A1 | 11/2018 |
| WO | 2019046299 A1 | 3/2019 |
| WO | 2019063520 A1 | 4/2019 |
| WO | 2019074938 A1 | 4/2019 |
| WO | 2019102846 A1 | 5/2019 |
| WO | 2019204406 A1 | 10/2019 |
| WO | 2019241659 A1 | 12/2019 |
| WO | 2021052850 A1 | 3/2021 |
| WO | 2021069338 A1 | 4/2021 |
| WO | 2021069343 A1 | 4/2021 |
| WO | 2021197996 A1 | 10/2021 |

OTHER PUBLICATIONS

Choi; Jun-Ho et al, "EmbraceNet: A robust deep learning architecture for multimodal classification", Information Fusion, 2019, 51, 259-270.

Gong Enhao; et al, "Deep Learning Enables Reduced Gadolinium Dose for Contrast-Enhanced Brain MRI", J. Magn. Reson. Imaging, 2018, 48, 330-340.

"Information on Primovist", 2016.

(56) References Cited

OTHER PUBLICATIONS

"International Preliminary Report on Patentability from PCT Application No. PCT/EP2020/077767", dated Apr. 12, 2022.
"Introduction to Multimodal Learning Model", DEV Community, Feb. 5, 2019.
Rajpurkar; Pranav et al, "CheXNet: Radiologist-Level Pneumonia Detection on Chest X-Rays with Deep Learning", 2017.
Yasaka Koichiro; et al, "Deep Learning with Convolutional Neural Network for Differentiation of Liver Masses at Dynamic Contrast-enhanced CT: A Preliminary Study", Radiology, Mar. 2018, vol. 286; No. 3, 887-896.
"International Preliminary Report on Patentability from PCT Application No. PCT/EP2020/075593", dated Mar. 31, 2022.
"International Preliminary Report on Patentability from PCT Application No. PCT/IB2020/058688", dated Mar. 31, 2022.
Kwon; et al, "Differentiation of small (less than or equal to cm) hepatocellular carcinomas from small benign nodules in cirrhotic liver on gadoxetic acid-enhanced and diffusion-weighted magnetic resonance images", Abdominal Imaging, Jul. 6, 2014, pp. 64-78.
Shtern; Alon, "Shape Correspondence Using Spectral Methods and Deep Learning Research Thesis", Aug. 2017.
Weizman; et al, "Prediction of Brain MR Scans in Longitudinal Tumor Follow-Up Studies", Oct. 1, 2012, pp. 179-187.
Baccouche; et al, "Sequential Deep Learning for Human Action Recognition", International Workshop on Human Behavior Understanding, 2011, 29-39.
Caraiani; et al, "Description of Focal Liver Lesions With GD-EOB-DTPA Enhanced MRI", Clujul Medical, 2015, vol. 88 No. 4, 438-448.
Chiusano; et al, "DCE-MRI Analysis Using Sparse Adaptive Representations", 2011, 67-74.
Frydrychowicz; et al, "Hepatobiliary MR Imaging with Gadolinium Based Contrast Agents", J Magn Reson Imaging, Mar. 2012, 35 (3), 492-511.
Ghodasara; Satyam et al, "Quantifying Perfusion Properties with DCE-MRI Using a Dictionary Matching Approach", International Society For Magnetic Resonance In Medicine, ISMRM,, Jun. 1, 2018.
"International Preliminary Report on Patentability from PCT Application No. PCT/IB2020/058688", dated Dec. 9, 2020.
Ji; et al, "3D Convolutional Neural Networks for Human Action Recognition", IEEE Transactions on Pattern Analysis and Machine Intelligence, Jan. 2013, vol. 35 No. 1, 221-231.
Karpathy; et al, "Large-scale Video Classification with Convolutional Neural Networks", Proceedings of the IEEE Conference on Computer Vision and Pattern Recognition, 2014, 1725-1732.
Khan; et al, "Chapter 3.3 "Neural Networks Basics"", A Guide to Convolutional Neural Networks for Computer Vision, Morgan & Claypool Publishers, 2018, pp. 36-39.
Kim; et al, "Arterial subtraction images of gadoxetate-enhanced MRI improve diagnosis of early-stage hepatocellular carcinoma", Journal of Hepatology, 2019, vol. 71, 534-542.
Simonyan; et al, "Two-Stream Convolutional Networks for Action Recognition in Videos", Advances in Neural Information Processing Systems, 2013, 568-576.
Thompson; et al, "Indicator Transit Time Considered as a Gamma Variate", Circulation Research, Jun. 1964, vol. XIV, 502-515.
Bannas; et al, "Combined Gadoxetic Acid and Gadofosveset Enhanced Liver MRI: A Feasibility and Parameter Optimization Study", Magnetic Resonance in Medicine, 2016, 75, 318-328.
Baytas Inci M.; et al, "Patient Subtyping via Time-Aware LSTM Networks", 2017.
Cannella; et al, "Common pitfalls when using the Liver Imaging Reporting and Data System (LI-RADS): lessons learned from a multi-year experience", Abdominal Imaging, Aug. 2, 2018, 43-53.
Conversano; et al, "Hepatic Vessel Segmentation for 3D Planning of Liver Surgery: Experimental Evaluation of a New Fully Automatic Algorithm", Academic Radiology, Apr. 2011, vol. 18/ No. 4, 461-470.

Fischer; et al, "Ultra-high-field imaging of the biliary tract of 7 Tesla: initial results of Gd-EOB-DTPA-enhanced MRCP", Proc. Intl. Soc. Mag. Reson. Med., 2012, 20.
Hope; et al, "Improvement of Gadoxetate Arterial Phase Capture With a High Spatio-Temporal Resolution Multiphase Three-Dimensional SPGR-Dixon Sequence", Journal of Magnetic Resonance Imaging, 2013, 38, 938-945.
Huang Gao.; et al, "Densely Connected Convolutional Networks", Jan. 28, 2018.
"International Preliminary Report on Patentability from PCT Application No. PCT/EP2020/075288", dated Mar. 31, 2022.
"International Preliminary Report on Patentability from PCT Application No. PCT/EP2020/077775", dated Apr. 12, 2022.
Kim; et al, "Gadoxetic acid-enhanced magnetic resonance imaging: Hepatocellular carcinoma and mimickers", Clinical and Molecular Hepatology, Sep. 2019, vol. 25 No. 3, 223-233.
Knobloch; et al, "Combined Gadoxetic Acid and Gadobenate Dimeglumine Enhanced Liver MRI for Liver Metastasis Detection: A Parameter Optimization Study", Proc. Intl. Soc. Mag. Reson. Med., 2018.
Le; Quoc V., "A Tutorial on Deep Learning Part 2: Autoencoders, Convolutional Neural Networks and Recurrent Neural Networks", Oct. 20, 2015.
Marcan; et al, "Segmentation of hepatic vessels from MRI images for planning of electroporation-based treatments in the liver", Radiol. Oncol., 2014, 48 (3), 267-281.
Meng Qinxue; et al, "Relational Autoencoder for Feature Extraction", Feb. 9, 2018.
Moccia; et al, "Blood vessel segmentation algorithms—Review of methods, datasets and evaluation metrics", Computer Methods and Programs in Biomedicine, 2018, 158, 71-91.
Coulden; Richard, "State-of-the-Art Imaging Techniques in Chronic Thromboembolic Pulmonary Hypertension", Proceedings of the American Thoracic Society, 2006, vol. 3, 577-583.
Delcroix Marion; et al, "Chronic Thromboembolic Pulmonary Hypertension; Epidemiology and Risk Factors", Annals of the American Thoracic Society, Jul. 2016, vol. 13 Supp. 13, S201-S206.
"FDA Reclassification Letter regarding OsteoDetect", May 24, 2018.
Galie Nazzareno; et al, "2015 ESC/ERS Guidelines for the diagnosis and treatment of pulmonary hypertension", European Heart Journal, Jan. 2016, vol. 37, Issue 1, 67-119.
Hachulla; et al, "Dual-energy computed tomographic imaging of pulmonary hypertension", Swiss Medical Weekly, 2016, 146; w14328, 1-20.
"International Preliminary Report on Patentability from PCT Application No. PCT/US2020/021861", dated Sep. 23, 2021.
Smith; Dana, "Artificial Intelligence Can Detect Alzheimer's Disease in Braine Scans Six Years Before a Diagnosis", Jan. 2, 2019.
Tapson Victor; et al, "Incidence and Prevalence of Chronic Thromboembolic Pulmonary Hypertension", Proceedings of the American Thoracic Society, Sep. 7, 2006, vol. 3, 564-567.
Wang; et al, "Stacked Fully Convolutional Networks for Pulmonary Vessel Segmentation", IEEE Visual Communications and Image Processing (VCIP), 2018.
Chibuzo, Abonyi et al., Intravascular Contrast Media in Radiography: Historical Development & Review of Risk Factors for Adverse Reactions, South American Journal of Clinical Research, 2016, Vo. 3, Issue 1.
He, et al., "Deep Predictive Modeling of Dynamic Contrast-Enhanced MRI Data", Proc. Intl. Soc. Mag. Reson. Med., 2019, vol. 27.
Ignee, Andre et al., Ultrasound contrast agents, Endoscopic Ultrasound, Nov.-Dec. 2016, vol. 5, Issue 6, 355-362.
Karani Neerav et al: "Temporal Interpolation of Abdominal MRIs Acquired During Free-Breathing", 4. Sep. 2017 (Sep. 4, 2017), 12th European Conference On Computer Vision, ECCV 2012; [Lecture Notes in Computer Science], Springer Berlin Heidelberg, Berlin, Heidelberg, pp. 359-367, XP047528114, ISSN: 0302-9743 ISBN: 978-3-642-39453-9.
Kurozumi, et al., "Evaluation of hemodynamic imaging findings of hypervascular hepatocellular carcinoma: comparison between dynamic contrast-enhanced magnetic resonance imaging using radial volu-

(56) References Cited

OTHER PUBLICATIONS metric imaging breath-hold examination with k-space-weighted image contrast reconstruction and dynamic computed tomography during hepatic arteriography", Japanese Journal of Radiology, 2018, pp. 295-302, vol. 36.

Lusic Hrvoje, et al., X-Ray Computed Tomography Contrast Agents, Chem. Rev., 2013.

Nouh Mohamed, et al., Radiographic and magnetic resonances contrast agents: Essentials and tips for safe practices, World Journal of Radiology, Sep. 28, 2017, vol. 9, Issue 9, 339-349.

Qin Chen et al.: "Convolutional Recurrent Neural Networks for Dynamic MR Image Reconstruction", IEEE Transactions On Medical Imaging, IEEE Service Center, Piscataway, NJ, US, Bd. 38, Nr. 1, Jan. 1, 2019 (Jan. 1, 2019), Seiten 280-290, P011694961, ISSN: 0278-0062, DOI: 10.1109/TMI.2018.2863670.

Smits Loek, et al., Evaluation of ultrasmall superparamagnetic iron-oxide (USPIO) enhanced MRI with ferumoxytol to quantify arterial wall inflammation, Atherosclerosis, 2017, 263, 211-218.

Takeshima, Hidenori: "Integrating Spatial and Temporal Correlations into a Deep Neural Network for Low-delay Reconstruction of Highly Undersampled Radial Dynamic Images", International Society for Magnetic Resonance in Medicine, ISMRM, 2030 Addison Street, 7th Floor, Berkeley, CA 94704 USA, pp. 2796, Jun. 1, 2018 (Jun. 1, 2018).

Written Opinion from PCT Application No. PCT/EP2021/057689, dated Jun. 24, 2021.

Xiao Yu-dong et al., MRI contrast agents: Classification and application (Review), International Journal of Molecular Medicine, 2016, 38, 1319-1326.

Zhang, et al., "Dynamic contrast enhanced MR imaging for evaluation of angiogenesis of hepatocellular nodules in liver cirrhosis in N-nitrosodiethylamine induced rat model", Eur. Radiol., 2017, pp. 2086-2094, vol. 27.

\* cited by examiner

SYSTEM, METHOD, AND COMPUTER PROGRAM PRODUCT FOR PREDICTING, ANTICIPATING, AND/OR ASSESSING TISSUE CHARACTERISTICS

CROSS REFERENCE TO RELATED APPLICATIONS

The present application is a U.S. national phase application under 35 U.S.C. § 371 of PCT International Application No. PCT/IB2020/058688, filed 17 Sep. 2020, and claims priority to EP Application No. 19197989.7, filed 18 Sep. 2019, and U.S. Provisional Patent Application No. 62/943,969, filed 5 Dec. 2019, the disclosures of which are incorporated herein in their entirety.

BACKGROUND

1. Field

The present disclosure relates generally to diagnostic imaging and, in some non-limiting embodiments or aspects, to predicting, anticipating, and/or assessing later phases of medical images and/or tissue characteristics from selected phases.

2. Technical Considerations

Magnetic resonance imaging, MRI for short, is an imaging method which is used especially in medical diagnostics for depicting structure and function of the tissue and organs in the human or animal body.

In MRI, the magnetic moments of protons in an examination object are aligned in a basic magnetic field, with the result that there is a macroscopic magnetization along a longitudinal direction. This is subsequently deflected from the resting position by the incident radiation of high-frequency (HF) pulses (excitation). The return of the excited states into the resting position (relaxation) or the magnetization dynamics is subsequently detected by means of one or more HF receiver coils as relaxation signals.

For spatial encoding, rapidly switched magnetic gradient fields are superimposed on the basic magnetic field. The captured relaxation signals or the detected and spatially resolved MRI data are initially present as raw data in a spatial frequency space, and can be transformed by subsequent Fourier transformation into the real space (image space).

In the case of native MRI, the tissue contrasts are generated by the different relaxation times (T1 and T2) and the proton density.

T1 relaxation describes the transition of the longitudinal magnetization into its equilibrium state, T1 being that time that is required to reach 63.21% of the equilibrium magnetization prior to the resonance excitation. It is also called longitudinal relaxation time or spin-lattice relaxation time.

Analogously, T2 relaxation describes the transition of the transversal magnetization into its equilibrium state.

MRI contrast agents develop their action by altering the relaxation times of the structures which take up contrast agents. A distinction can be made between two groups of substances: paramagnetic and superparamagnetic substances. Both groups of substances have unpaired electrons which induce a magnetic field around the individual atoms or molecules.

Superparamagnetic contrast agents lead to a predominant shortening of T2, whereas paramagnetic contrast agents mainly lead to a shortening of T1. A shortening of the T1 time leads to an increase in the signal intensity in T1-weighted MRI images, and a shortening of the T2 time leads to a decrease in the signal intensity in T2-weighted MRI images.

The action of said contrast agents is indirect, since the contrast agent itself does not give off a signal, but instead only influences the signal intensity of the hydrogen protons in its surroundings.

Extracellular, intracellular and intravascular contrast agents can be distinguished according to their pattern of spreading in the tissue.

An example of a superparamagnetic contrast agent are iron oxide nanoparticles (SPIO: superparamagnetic iron oxide). Superparamagnetic contrast agents are commonly used as intravascular agents.

Examples of paramagnetic contrast agents are gadolinium chelates such as gadopentetate dimeglumine (trade name: Magnevist® and others), gadobenate dimeglumine (trade name: Multihance®), gadoteric acid (Dotarem®, Dotagita®, Cyclolux®), gadodiamide (Omniscan®), gadoteridol (ProHance®) and gadobutrol (Gadovist®).

Extracellular, intracellular and intravascular contrast agents can be distinguished according to their pattern of spreading in the tissue.

In CT, contrast agents absorb the X-ray radiation created by the CT machine as the X-ray radiation passes through the patient. In nuclear medicine, a form of molecular imaging, the contrast agent includes radioactive atoms which decay to produce a signal which is detected by the imaging equipment. In hyperpolarized MRI, the majority of nuclei are aligned with a magnetic field and injected into the patient for imaging.

Contrast agents based on gadoxetic acid are characterized by specific uptake by liver cells, the hepatocytes, by enrichment in the functional tissue (parenchyma) and by enhancement of the contrasts in healthy liver tissue. The cells of cysts, metastases and most liver-cell carcinomas no longer function like normal liver cells, do not take up the contrast agent or hardly take it up, are not depicted with enhancement, and are identifiable and localizable as a result.

Examples of contrast agents based on gadoxetic acid are described in U.S. Pat. No. 6,039,931A; they are commercially available under the trade names Primovist® or Eovist® for example.

The contrast-enhancing effect of Primovist®/Eovist® is mediated by the stable gadolinium complex Gd-EOB-DTPA (gadolinium ethoxybenzyl diethylenetriaminepentaacetic acid). DTPA forms, with the paramagnetic gadolinium ion, a complex which has an extremely high thermodynamic stability. The ethoxybenzyl radical (EOB) is the mediator of the hepatobiliary uptake of the contrast agent.

Primovist® can be used for the detection of tumours in the liver. Blood supply to the healthy liver tissue is primarily achieved via the portal vein (vena portae), whereas the liver artery (arteria hepatica) supplies most primary tumours. After intravenous injection of a bolus of contrast agent, it is accordingly possible to observe a time delay between the signal rise of the healthy liver parenchyma and of the tumour. Besides malignant tumours, what are frequently found in the liver are benign lesions such as cysts, haemangiomas and focal nodular hyperplasias (FNH). A proper planning of therapy requires that these be differentiated from the malignant tumours. Primovist® can be used for the identification of benign and malignant focal liver lesions. By means of T1-weighted MRI, it provides information about the character of said lesions. Differentiation is achieved by making use of the different blood supply to liver and tumour and of the temporal profile of contrast enhancement.

The contrast enhancement achieved by means of Primovist® can be divided into at least two phases: into a dynamic phase (comprising the so-called arterial phase, portal-vein phase and late phase) and the hepatobiliary phase, in which a significant uptake of Primovist® into the hepatocytes has already taken place.

In the case of the contrast enhancement achieved by Primovist® during the distribution phase, what are observed are typical perfusion patterns which provide information for the characterization of the lesions. Depicting the vascularization helps to characterize the lesion types and to determine the spatial relationship between tumour and blood vessels.

In the case of T1-weighted MRI images, Primovist® leads, 10-20 minutes after the injection (in the hepatobiliary phase), to a distinct signal enhancement in the healthy liver parenchyma, whereas lesions containing no hepatocytes or only a few hepatocytes, for example metastases or moderately to poorly differentiated hepatocellular carcinomas (HCCs), appear as darker regions.

Tracking the spreading of the contrast agent over time across the dynamic phase and the hepatobiliary phase provides a good possibility of the detection and differential diagnosis of focal liver lesions; however, the examination extends over a comparatively long time span. Over said time span, movements by the patient should be avoided in order to minimize movement artefacts in the MRI image. The lengthy restriction of movement can be unpleasant for a patient and difficult to consistently achieve in practice.

SUMMARY

Non-limiting embodiments or aspects of the present disclosure are directed to improvement of diagnostic imaging examinations, for example in the acceleration or the shortening of scan time (e.g., for the detection and differential diagnosis of focal liver lesions by means of dynamic contrast-enhancing magnetic resonance imaging (MRI), etc.). Non-limiting embodiments or aspects of the present disclosure provide methods, systems, and computer program products for predicting, anticipating, and/or assessing later phases of medical images from selected (e.g., earlier, etc.) phases, for example of the liver during the hepatobiliary phase, thereby reducing an image data acquisition time. Additionally, or alternatively, parameters may be determined using data from an imaging sequence which may replace and/or be used to synthesize later images, for example pharmacokinetic parameters of a volume of tissue (e.g., of a voxel, etc.).

Although described primarily with respect to MRI of liver tissue with contrast, non-limiting embodiments or aspects of the present disclosure are not limited thereto, and methods, systems, and computer program products according to non-limiting embodiments or aspects may predict, anticipate, and/or assess later phases of medical images from selected (e.g., earlier, etc.) phases of medical images of any organ acquired using any imaging modality with or without contrast agent.

According to some non-limiting embodiments or aspects, provided is a method comprising the steps of receiving a plurality of MRI images, the MRI images showing an examination region during a first time span, feeding the plurality of MRI images to a prediction model, the prediction model having been trained by means of supervised learning to predict, on the basis of MRI images showing an examination region during a first time span, one or more MRI images showing the examination region during a second time span, generating one or more predicted MRI images showing the examination region during a second time span by means of the prediction, and displaying and/or outputting the one or more predicted MRI images and/or storing the one or more predicted MRI images in a data storage medium.

According to some non-limiting embodiments or aspects, provided is a system comprising a receiving unit, a control and calculation unit, and an output unit, the control and calculation unit being configured to prompt the receiving unit to receive a plurality of MRI images, the received MRI images showing an examination region during a first time span, the control and calculation unit being configured to predict one or more MRI images on the basis of the received MRI images, the one or more predicted MRI images showing the examination region during a second time span, the control and calculation unit being configured to prompt the output unit to display the one or more predicted MRI images, to output them or to store them in a data storage medium.

According to some non-limiting embodiments or aspects, provided is a computer program product comprising a computer program which can be loaded into a memory of a computer, where it prompts the computer to execute the following steps: receiving a plurality of MRI images, the MRI images showing an examination region during a first time span, feeding the received MRI images to a prediction model, the prediction model having been trained by means of supervised learning to predict, on the basis of MRI images showing an examination region during a first time span, one or more MRI images showing the examination region during a second time span, receiving one or more predicted MRI images showing the examination region during a second time span, as output from the prediction model, displaying and/or outputting the one or more predicted MRI images and/or storing the one or more predicted MRI images in a data storage medium.

According to some non-limiting embodiments or aspects, provided is a use of a contrast agent in an MRI method, the MRI method comprising the following steps: administering the contrast agent, the contrast agent spreading in an examination region, generating a plurality of MRI images of the examination region during a first time span, feeding the generated MRI images to a prediction model, the prediction model having been trained by means of supervised learning to predict, on the basis of MRI images showing an examination region during a first time span, one or more MRI images showing the examination region during a second time span, receiving one or more predicted MRI images showing the examination region during a second time span, as output from the prediction model, and displaying and/or outputting the one or more predicted MRI images and/or storing the one or more predicted MRI images in a data storage medium.

According to some non-limiting embodiments or aspects, provided is a contrast agent for use in an MRI method, the MRI method comprising the following steps: administering a contrast agent, the contrast agent spreading in an examination region, generating a plurality of MRI images of the examination region during a first time span, feeding the generated MRI images to a prediction model, the prediction model having been trained by means of supervised learning to predict, on the basis of MRI images showing an examination region during a first time span, one or more MRI images showing the examination region during a second time span, receiving one or more predicted MRI images showing the examination region during a second time span, as output from the prediction model, displaying and/or outputting the one or more predicted MRI images and/or storing the one or more predicted MRI images in a data storage medium.

Further provided is a kit comprising a contrast agent and a computer program product according to non-limiting embodiments or aspects of the present disclosure.

Non-limiting embodiments or aspects of the present disclosure are more particularly elucidated below without distinguishing between the subjects of embodiments (method, system, computer program product, use, contrast agent for use, kit). On the contrary, the following elucidations are intended to apply analogously to all the subjects of all embodiments, irrespective of in which context (method, system, computer program product, use, contrast agent for use, kit) they occur.

If steps are stated in an order in the present description or in the claims, this does not necessarily mean that embodiments or aspects are restricted to the stated order. On the contrary, it is conceivable that the steps are also executed in a different order or else in parallel to one another, unless one step builds upon another step, this absolutely requiring that the building step be executed subsequently (this being, however, clear in the individual case). The stated orders may thus be preferred embodiments.

Non-limiting embodiments or aspects of the present disclosure shorten the time span of the examination of an examination object in the generation of MRI images. In some non-limiting embodiments or aspects, this is achieved by MRI images of an examination region of the examination object being measured in a first time span (magnetic resonance measurement), and the measured MRI images then being used to predict, with the aid of a self-learning algorithm, one or more MRI images showing the examination region in a second time span. The actual magnetic resonance measurement on the examination object is thus restricted to the first time span and does not encompass the second time span. The MRI images showing the examination region during the first time span contain information allowing a prediction for the second time span.

The "examination object" may usually be a living being, preferably a mammal, very particularly preferably a human. The examination region may be a portion of the examination object, for example an organ or a portion of an organ. In a non-limiting embodiment or aspect, the examination region is the liver or a portion of the liver of a mammal (e.g., a human).

The "examination region", also called image volume (field of view, FOV), may be in particular a volume which is imaged in the magnetic resonance images. Generally, a 3-dimensional field of view may be said to consist of one or more volume elements or voxels. If a 2-dimensional FOV is being considered, it may be said to consist of 1 or more voxels or 1 or more pixels (picture elements.) The examination region may be typically defined by a radiologist, for example on an overview image (localizer). It is self-evident that the examination region can, alternatively or additionally, also be defined automatically, for example on the basis of a selected protocol.

The examination region is introduced into a basic magnetic field. The examination region is subjected to an MRI method and this generates a plurality of MRI images showing the examination region during a first time span.

The term plurality means that at least two MRI images or measurements, preferably at least three, very particularly preferably at least four MRI images or measurements are generated.

A contrast agent which spreads in the examination region is administered to the examination object. The contrast agent is preferably administered intravenously as a bolus, in a weight-adapted manner.

A "contrast agent" is understood to mean a substance or substance mixture, the presence of which in a magnetic resonance measurement leads to an altered signal. Preferably, the contrast agent leads to a shortening of the T1 relaxation time and/or of the T2 relaxation time.

Preferably, the contrast agent is a hepatobiliary contrast agent such as, for example, Gd-EOB-DTPA or Gd-BOPTA.

In a particularly preferred embodiment, the contrast agent is a substance or a substance mixture with gadoxetic acid or a gadoxetic acid salt as contrast-enhancing active substance. Very particular preference is given to the disodium salt of gadoxetic acid (Gd-EOB-DTPA disodium).

Preferably, the first time span starts before the administration of the contrast agent or with the administration of the contrast agent. It is advantageous when one or more MRI images showing the examination region without contrast agent are generated, since a radiologist can already gain important information about the state of health of the examination object in such images. For example, a radiologist can identify bleedings in such native MRI images.

The first time span preferably encompasses the contrast agent distributing in the examination region. Preferably, the first time span encompasses the arterial phase and/or the portal-vein phase and/or the late phase in the dynamic contrast-enhancing magnetic resonance tomography of a liver or a portion of a liver of an examination object. The stated phases are, for example, defined and described in the following publications: J. Magn. Reson. Imaging, 2012, 35(3): 492-511, doi:10.1002/jmri.22833; Clujul Medical, 2015, Vol. 88 no. 4: 438-448, DOI: 10.15386/cjmed-414; Journal of Hepatology, 2019, Vol. 71: 534-542, http://dx.doi.org/10.1016/j.jhep.2019.05.005.

In a preferred embodiment, the first time span is chosen such that such MRI images of the liver or a portion of the liver of an examination object are generated,
  showing the examination region without contrast agent,
  showing the examination region during the arterial phase, in which the contrast agent spreads in the examination region via the arteries,
  showing the examination region during the portal-vein phase, in which the contrast agent reaches the examination region via the portal vein, and
  showing the examination region during the late phase, in which the concentration of the contrast agent in the arteries and veins declines and the concentration of the contrast agent in the extravascular tissue and/or liver cells rises.

Preferably, the first time span starts within a time span of from one minute to one second before the administration of the contrast agent, or with the administration of the contrast agent, and lasts for a time span of from 2 minutes to 15 minutes, preferably 2 minutes to 13 minutes, yet more preferably 3 minutes to 10 minutes, from the administration of the contrast agent. Since the contrast agent is renally and/or biliarily excreted very slowly, the broad time span can extend up to two hours or more after the administration of the contrast agent.

Since contrast agent can spread with varying rapidity in different examination objects, the first time span can also be defined via the concentrations of the contrast agent in the different areas of the examination region. One possibility is depicted in FIG. 1.

FIG. 1 shows schematically the temporal profile of the concentrations of contrast agent in the liver arteries (A), the liver veins (V) and the healthy liver cells (P). The concentrations are depicted in the form of the signal intensities I in the stated areas (liver arteries, liver veins, liver cells) in the magnetic resonance measurement as a function of the time t. Upon an intravenous bolus injection, the concentration of the contrast agent rises in the liver arteries (A) first of all (dashed curve). The concentration passes through a maximum and then drops. The concentration in the liver veins (V) rises more slowly than in the liver arteries and reaches its maximum later (dotted curve). The concentration of the contrast agent in the healthy liver cells (P) rises slowly (continuous curve) and reaches its maximum only at a very much later time point (not depicted in FIG. 1). A few characteristic time points can be defined: At time point TP0, contrast agent is administered intravenously as a bolus. At time point TP1, the concentration (the signal intensity) of the contrast agent in the liver arteries reaches its maximum. At time point TP2, the curves of the signal intensities for the liver arteries and the liver veins intersect. At time point TP3, the concentration (the signal intensity) of the contrast agent in the liver veins passes through its maximum. At time point TP4, the curves of the signal intensities for the liver arteries and the liver cells intersect. At time point T5, the concentrations in the liver arteries and the liver veins have dropped to a level at which they no longer cause a measurable contrast enhancement.

In a preferred embodiment, the first time span encompasses at least the time points TP0, TP1, TP2, TP3 and TP4.

In a preferred embodiment, at least MRI images of all the following phases are generated (by measurement): in the time span from TP0 to TP1, in the time span from TP1 to TP2, in the time span from TP2 to TP3 and in the time span TP3 to TP4.

It is conceivable that, in the time spans TP0 to TP1, TP1 to TP2, TP2 to TP3, TP3 to TP4, one or more MRI images are generated (by measurement) in each case. It is also conceivable that, during one or more time spans, sequences of MRI images are generated (by measurement).

The term sequence means a chronological order, i.e. what are generated are multiple MRI images showing the examination region at successive time points.

A time point is assigned to each MRI image or a time point can be assigned to each MRI image. Usually, this time point is the time point at which the MRI image has been generated (absolute time). A person skilled in the art is aware that the generation of an MRI image uses a certain time span. What can be assigned to an MRI image is, for example, the time point of the start of acquisition or the time point of the completion of acquisition. However, it is also conceivable that arbitrary time points are assigned to the MRI images (e.g. relative time points).

On the basis of a time point, an MRI image can be arranged chronologically with respect to another MRI image; on the basis of the time point of an MRI image, it is possible to establish whether the moment shown in the MRI image took place chronologically before or chronologically after a moment shown in another MRI image.

Preferably, the MRI images are chronologically ordered in a sequence and a plurality such that MRI images showing an earlier state of the examination region are arranged in the sequence and the plurality before those MRI images showing a later state of the examination region.

The time span between two MRI images immediately following one another in a sequence and/or plurality is preferably identical for all pairs of MRI images immediately following one another in the sequence and/or plurality, i.e. the MRI images were preferably generated with a constant acquisition rate.

On the basis of the MRI images generated (by measurement) during the first time span, one MRI image is predicted or multiple MRI images are predicted which show the examination region during a second time span.

In some non-limiting embodiments or aspects, the second time span follows the first time span.

The second time span is preferably a time span within the hepatobiliary phase; preferably a time span which starts at least 10 minutes after administration of the contrast agent, preferably at least 20 minutes after administration of the contrast agent.

The plurality of measured MRI images showing the examination region during the first time span is fed to a prediction model. The prediction model is a model configured to predict, on the basis of a plurality of MRI images showing an examination region during a first time span, one or more MRI images showing the examination region during a second time span.

In this connection, the term "prediction" means that the MRI images showing the examination region during the second time span are calculated using the MRI images showing the examination region during the first time span.

The prediction model was preferably created with the aid of a self-learning algorithm in a supervised machine learning process. Learning is achieved by using training data comprising a multiplicity of MRI images of the first and the second time span.

The self-learning algorithm generates, during machine learning, a statistical model which is based on the training data. This means that the examples are not simply learnt by heart, but that the algorithm "recognizes" patterns and regularities in the training data. The prediction model can thus also assess unknown data. Validation data can be used to test the quality of the assessment of unknown data.

The prediction model is trained by means of supervised learning, i.e. pluralities of MRI images from the first time span are presented successively to the algorithm and it is informed of which MRI images in the second time span are associated with these pluralities. The algorithm then learns a relationship between the pluralities of MRI images of the first time span and the MRI images of the second time span in order to predict one or more MRI images in the second time span for unknown pluralities of MRI images of the first time span.

Self-learning systems trained by means of supervised learning are widely described, for example, C. Perez: *Machine Learning Techniques: Supervised Learning and Classification*, Amazon Digital Services LLC—Kdp Print Us, 2019, ISBN 1096996545, 9781096996545.

Preferably, the prediction model is an artificial neural network.

Such an artificial neural network comprises at least three layers of processing elements: a first layer with input neurons (nodes), an N-th layer with at least one output neuron (nodes) and N−2 inner layers, where N is a natural number and greater than 2.

The input neurons serve to receive digital MRI images as input values. Normally, there is one input neuron for each pixel or voxel of a digital MRI image. There can be additional input neurons for additional input values (e.g.

information about the examination region, about the examination object and/or about conditions which prevailed when generating the MRI images).

In such a network, the output neurons serve to predict one or more MRI images of a second time span for a plurality of MRI images of a first time span.

The processing elements of the layers between the input neurons and the output neurons are connected to one another in a predetermined pattern with predetermined connection weights.

Preferably, the artificial neural network is a so-called convolutional neural network (CNN for short).

A convolutional neural network is capable of processing input data in the form of a matrix. This makes it possible to use digital MRI images depicted as a matrix (e.g. width× height×colour channels) as input data. By contrast, a normal neural network, for example in the form of a multilayer perceptron (MLP), requires a vector as input, i.e. to use an MRI image as input, the pixels or voxels of the MRI image would have to be rolled out successively in a long chain. As a result, normal neural networks are, for example, not capable of recognizing objects in an MRI image independently of the position of the object in the MRI image. The same object at a different position in the MRI image would have a completely different input vector.

A CNN consists essentially of filters (convolutional layer) and aggregation layers (pooling layer) which are repeated alternately and, at the end, of one layer or multiple layers of "normal" completely connected neurons (dense/fully connected layer).

When analysing sequences (sequences of MRI image), space and time can be treated as equivalent dimensions and, for example, processed via 3D folds. This has been shown in the papers by Baccouche et al. (*Sequential Deep Learning for Human Action Recognition; International Workshop on Human Behavior Understanding*, Springer 2011, pages 29-39) and Ji et al. (3*D Convolutional Neural Networks for Human Action Recognition*, IEEE Transactions on Pattern Analysis and Machine Intelligence, 35(1), 221-231). Furthermore, it is possible to train different networks which are responsible for time and space and to lastly merge the features, as described in publications by Karpathy et al. (*Large-scale Video Classification with Convolutional Neural Networks*; Proceedings of the IEEE conference on Computer Vision and Pattern Recognition, 2014, pages 1725-1732) and Simonyan & Zisserman (*Two-stream Convolutional Networks for Action Recognition in Videos*; Advances in Neural Information Processing Systems, 2014, pages 568-576).

Recurrent neural networks (RNNs) are a family of so-called feedforward neural networks which contain feedback connections between layers. RNNs allow the modelling of sequential data by common utilization of parameter data via different parts of the neural network. The architecture for an RNN contains cycles. The cycles represent the influence of a current value of a variable on its own value at a future time point, since at least a portion of the output data from the RNN is used as feedback for processing subsequent inputs in a sequence. Details can be gathered from, for example: S. Khan et al.: *A Guide to Convolutional Neural Networks for Computer Vision*, Morgan & Claypool Publishers 2018, ISBN 1681730227, 9781681730226.

The training of the neural network can, for example, be carried out by means of a backpropagation method. In this connection, what is striven for, for the network, is a mapping of given input vectors onto given output vectors that is as reliable as possible. The mapping quality is described by an error function. The goal is to minimize the error function. In the case of the backpropagation method, an artificial neural network is taught by altering the connection weights.

In the trained state, the connection weights between the processing elements contain information regarding the relationship between the pluralities of MRI images of the first time span and the MRI images of the second time span that can be used in order to predict one or more MRI images showing an examination region during the second time span for new pluralities of MRI images showing the examination region during the first time span.

A cross-validation method can be used in order to divide the data into training and validation data sets. The training data set is used in the backpropagation training of network weights. The validation data set is used in order to check the accuracy of prediction with which the trained network can be applied to unknown pluralities of MRI images.

As already indicated, further information about the examination object, about the examination region and/or about examination conditions can also be used for training, validation and prediction.

Examples of information about the examination object are: sex, age, weight, height, anamnesis, nature and duration and amount of medicaments already ingested, blood pressure, central venous pressure, breathing rate, serum albumin, total bilirubin, blood sugar, iron content, breathing capacity and the like. These can, for example, also be gathered from a database or an electronic patient file.

Examples of information about the examination region are: pre-existing conditions, operations, partial resection, liver transplantation, iron liver, fatty liver and the like.

It is conceivable that the plurality of MRI images showing the examination region during the first time span are subjected to a movement correction before they are fed to the prediction model. Such a movement correction ensures that a pixel or voxel of a first MRI image shows the same examination region as the corresponding pixel or voxel of a second, temporally downstream MRI image. Movement correction methods are described in, for example: EP3118644, EP3322997, US20080317315, US20170269182, US20140062481, EP2626718.

A system according to non-limiting embodiments or aspects may execute a method according to non-limiting embodiments or aspects.

The system comprises a receiving unit, a control and calculation unit and an output unit.

It is conceivable that the stated units are components of a single computer system; however, it is also conceivable that the stated units are components of multiple separate computer systems which are connected to one another via a network in order to transmit data and/or control signals from one unit to another unit.

A "computer system" is a system for electronic data processing that processes data by means of programmable calculation rules. Such a system usually comprises a "computer", that unit which comprises a processor for carrying out logical operations, and also peripherals.

In computer technology, "peripherals" refer to all devices which are connected to the computer and serve for the control of the computer and/or as input and output devices. Examples thereof are monitor (screen), printer, scanner, mouse, keyboard, drives, camera, microphone, loudspeaker, etc. Internal ports and expansion cards are, too, considered to be peripherals in computer technology.

Computer systems of today are frequently divided into desktop PCs, portable PCs, laptops, notebooks, netbooks and tablet PCs and so-called handhelds (e.g. smartphone);

all these systems can be utilized for carrying out non-limiting embodiments or aspects of the present disclosure.

Inputs into the computer system are achieved via input means such as, for example, a keyboard, a mouse, a microphone and/or the like.

The system may be configured to receive pluralities of MRI images showing an examination region during a first time span and to generate (to predict, to calculate), on the basis of these data and optionally further data, one or more MRI images showing the examination region during a second time span.

The control and calculation unit serves for the control of the receiving unit, the coordination of the data and signal flows between various units, and the calculation of MRI images. It is conceivable that multiple control and calculation units are present.

The receiving unit serves for the receiving of pluralities of MRI images. The pluralities can, for example, be transmitted from a magnetic resonance system or be read from a data storage medium. The magnetic resonance system can be a component of the system. However, it is also conceivable that the system is a component of a magnetic resonance system.

The sequences of MRI images and optionally further data are transmitted from the receiving unit to the control and calculation unit.

The control and calculation unit is configured to predict, on the basis of the pluralities of MRI images showing an examination region during a first time span, one or more MRI images, the predicted MRI images showing the examination region during a second time span. Preferably, what can be loaded into a memory of the control and calculation unit is a prediction model which is used to calculate the MRI images of the second time span. The prediction model was preferably generated (trained) with the aid of a self-learning algorithm by means of supervised learning.

Via the output unit, the predicted MRI images can be displayed (e.g. on a screen), be outputted (e.g. via a printer) or be stored in a data storage medium.

Further non-limiting embodiments or aspects are set forth in the following numbered clauses:

Clause 1. A computer-implemented method comprising: obtaining measurement information associated with a parameter of a voxel of tissue of a patient measured at two or more time points, wherein the two or more time points occur before one or more characteristics of the voxel of the tissue are separable in an image generated based on the parameter of the voxel measured at a single time point of the two or more time points; and determining, based on the parameter of the voxel at the two or more time points, the one or more characteristics of the voxel of tissue.

Clause 2. The computer-implemented method of clause 1, wherein the one or more characteristics of the voxel of tissue are further determined based on information associated with at least one of the patient and a condition of the patient.

Clause 3. The computer-implemented method of any of clauses 1 and 2, wherein the one or more characteristics of the voxel of the tissue are determined for a time point corresponding to at least one the two or more time points.

Clause 4. The computer-implemented method of any of clauses 1-3, wherein the one or more characteristics of the voxel of tissue are determined for a time point subsequent to the two or more time points.

Clause 5. The computer-implemented method of any of clauses 1-4, further comprising: generating, based on the one or more characteristics, one or more images including the one or more characteristics of the voxel of tissue at the time point after the two or more time points.

Clause 6. The computer-implemented method of any of clauses 1-5, further comprising: determining that the measurement information associated with the parameter of the voxel of the tissue of the patient includes a threshold amount of measurement information associated with determining the one or more characteristics of the voxel of the tissue; and in response to determining that the measurement information includes the threshold amount of measurement information, controlling an imaging system to automatically stop acquisition of the measurement information.

Clause 7. The computer-implemented method of any of clauses 1-6, wherein determining the one or more characteristics includes: feeding the measurement information associated with the parameter of the voxel of the tissue of the patient to a prediction model, the prediction model having been trained by means of supervised learning to predict, on the basis the measurement information associated with the parameter at the two or more time points, the one or more characteristics of the voxel of the tissue.

Clause 8. The computer-implemented method of any of clauses 1-7, wherein determining the one or more characteristics includes: fitting a pharmacokinetic/pharmacodynamic (PK/PD) model of the voxel of the tissue to the parameter of the voxel of the tissue measured at the two or more time points; and determining, based on the PK/PD model fitted to the parameter of the voxel of the tissue measured at the two or more time points, the one or more characteristics of the voxel of the tissue.

Clause 9. The computer-implemented method of any of clauses 1-8, wherein determining the one or more characteristics includes: fitting a PK/PD curve of a plurality of plurality of PK/PD curves precomputed for the parameter to the parameter of the voxel of the tissue measured at the two or more time points; and determining, based on the PK/PD curve fitted to the parameter at the two or more time points, the one or more characteristics of the voxel of the tissue.

Clause 10. The computer-implemented method of any of clauses 1-9, wherein determining the one or more characteristics includes: approximating a curve representing the one or more characteristics of the voxel of the tissue with a set of basis functions; fitting the approximated curve to the parameter of the voxel of the tissue measured at the two or more time points; and determining, based on the approximated curve fitted to the parameter of the voxel of the tissue measured at the two or more time points, the one or more characteristics of the voxel of the tissue.

Clause 11. The computer-implemented method of any of clause 1-10, wherein determining the one or more characteristics includes: fitting a curve of a plurality of curves precomputed for the parameter with a set of basis functions to the parameter of the voxel of the tissue measured at the two or more time points; determining, based on the curve fitted to the parameter of the voxel of the tissue measured at the two or more time points, the one or more characteristics of the voxel of the tissue.

Clause 12. A system comprising: one or more processors programmed and/or configured to: obtain measurement information associated with a parameter of a voxel of tissue of a patient measured at two or more time points, wherein the two or more time points occur before one or more characteristics of the voxel of the tissue are separable in an image generated based on the parameter of the voxel measured at a single time point of the two or more time points;

and determine, based on the parameter of the voxel at the two or more time points, the one or more characteristics of the voxel of tissue.

Clause 13. The system of clause 12, wherein the one or more characteristics of the voxel of tissue are further determined based on information associated with at least one of the patient and a condition of the patient.

Clause 14. The system of any of clauses 12 and 13, wherein the one or more characteristics of the voxel of the tissue are determined for a time point corresponding to at least one the two or more time points.

Clause 15. The system of any of clauses 12-14, wherein the one or more characteristics of the voxel of tissue are determined for a time point subsequent to the two or more time points.

Clause 16. The system of any of clauses 12-15, wherein the one or more processors are further programmed and/or configured to: generate, based on the one or more characteristics, one or more images including the one or more characteristics of the voxel of tissue at the time point after the two or more time points.

Clause 17. The system of any of clauses 12-16, wherein the one or more processors are further programmed and/or configured to: determine that the measurement information associated with the parameter of the voxel of the tissue of the patient includes a threshold amount of measurement information associated with determining the one or more characteristics of the voxel of the tissue; and in response to determining that the measurement information includes the threshold amount of measurement information, control an imaging system to automatically stop acquisition of the measurement information.

Clause 18. The system of any of clauses 12-17, wherein the one or more processors are further programmed and/or configured to determine the one or more characteristics by: feeding the measurement information associated with the parameter of the voxel of the tissue of the patient to a prediction model, the prediction model having been trained by means of supervised learning to predict, on the basis the measurement information associated with the parameter at the two or more time points, the one or more characteristics of the voxel of the tissue.

Clause 19. The system of any of clauses 12-18, wherein the one or more processors are further programmed and/or configured to determine the one or more characteristics by: fitting a pharmacokinetic/pharmacodynamic (PK/PD) model of the voxel of the tissue to the parameter of the voxel of the tissue measured at the two or more time points; and determining, based on the PK/PD model fitted to the parameter of the voxel of the tissue measured at the two or more time points, the one or more characteristics of the voxel of the tissue.

Clause 20. The system of any of clauses 12-19, wherein the one or more processors are further programmed and/or configured to determine the one or more characteristics by: fitting a PK/PD curve of a plurality of plurality of PK/PD curves precomputed for the parameter to the parameter of the voxel of the tissue measured at the two or more time points; and determining, based on the PK/PD curve fitted to the parameter at the two or more time points, the one or more characteristics of the voxel of the tissue.

Clause 21. The system of any of clauses 12-20, wherein the one or more processors are further programmed and/or configured to determine the one or more characteristics by: approximating a curve representing the one or more characteristics of the voxel of the tissue with a set of basis functions; fitting the approximated curve to the parameter of the voxel of the tissue measured at the two or more time points; and determining, based on the approximated curve fitted to the parameter of the voxel of the tissue measured at the two or more time points, the one or more characteristics of the voxel of the tissue.

Clause 22. The system of any of clauses 12-21, wherein the one or more processors are further programmed and/or configured to determine the one or more characteristics by: fitting a curve of a plurality of curves precomputed for the parameter with a set of basis functions to the parameter of the voxel of the tissue measured at the two or more time points; determining, based on the curve fitted to the parameter of the voxel of the tissue measured at the two or more time points, the one or more characteristics of the voxel of the tissue.

Clause 23. A computer program product comprising at least one non-transitory computer-readable medium including program instructions that, when executed by at least one processor, cause the at least one processor to: obtain measurement information associated with a parameter of a voxel of tissue of a patient measured at two or more time points, wherein the two or more time points occur before one or more characteristics of the voxel of the tissue are separable in an image generated based on the parameter of the voxel measured at a single time point of the two or more time points; and determine, based on the parameter of the voxel at the two or more time points, the one or more characteristics of the voxel of tissue.

Clause 24. The computer program product of clause 23, wherein the one or more characteristics of the voxel of tissue are further determined based on information associated with at least one of the patient and a condition of the patient.

Clause 25. The computer program product of any of clauses 23 and 24, wherein the one or more characteristics of the voxel of the tissue are determined for a time point corresponding to at least one the two or more time points.

Clause 26. The computer program product of any of clauses 23-25, wherein the one or more characteristics of the voxel of tissue are determined for a time point subsequent to the two or more time points.

Clause 27. The computer program product of any of clauses 23-26, wherein the instructions further cause the at least one processor to: generate, based on the one or more characteristics, one or more images including the one or more characteristics of the voxel of tissue at the time point after the two or more time points.

Clause 28. The computer program product of any of clauses 23-27 wherein the instructions further cause the at least one processor to: determine that the measurement information associated with the parameter of the voxel of the tissue of the patient includes a threshold amount of measurement information associated with determining the one or more characteristics of the voxel of the tissue; and in response to determining that the measurement information includes the threshold amount of measurement information, control an imaging system to automatically stop acquisition of the measurement information.

Clause 29. The computer program product of any of clauses 23-28, wherein the instructions cause the at least one processor to determine the one or more characteristics by: feeding the measurement information associated with the parameter of the voxel of the tissue of the patient to a prediction model, the prediction model having been trained by means of supervised learning to predict, on the basis the measurement information associated with the parameter at the two or more time points, the one or more characteristics of the voxel of the tissue.

Clause 30. The computer program product of any of clauses 23-29, wherein the instructions cause the at least one processor to determine the one or more characteristics by: fitting a pharmacokinetic/pharmacodynamic (PK/PD) model of the voxel of the tissue to the parameter of the voxel of the tissue measured at the two or more time points; and determining, based on the PK/PD model fitted to the parameter of the voxel of the tissue measured at the two or more time points, the one or more characteristics of the voxel of the tissue.

Clause 31. The computer program product of any of clauses 23-30, wherein the instructions cause the at least one processor to determine the one or more characteristics by: fitting a PK/PD curve of a plurality of plurality of PK/PD curves precomputed for the parameter to the parameter of the voxel of the tissue measured at the two or more time points; and determining, based on the PK/PD curve fitted to the parameter at the two or more time points, the one or more characteristics of the voxel of the tissue.

Clause 32. The computer program product of any of clauses 23-31, wherein the instructions cause the at least one processor to determine the one or more characteristics by: approximating a curve representing the one or more characteristics of the voxel of the tissue with a set of basis functions; fitting the approximated curve to the parameter of the voxel of the tissue measured at the two or more time points; and determining, based on the approximated curve fitted to the parameter of the voxel of the tissue measured at the two or more time points, the one or more characteristics of the voxel of the tissue.

Clause 33. The computer program product of any of clauses 23-32, wherein the instructions cause the at least one processor to determine the one or more characteristics by: fitting a curve of a plurality of curves precomputed for the parameter with a set of basis functions to the parameter of the voxel of the tissue measured at the two or more time points; determining, based on the curve fitted to the parameter of the voxel of the tissue measured at the two or more time points, the one or more characteristics of the voxel of the tissue.

BRIEF DESCRIPTION OF THE DRAWINGS

Additional advantages and details of embodiments or aspects of the present disclosure are explained in greater detail below with reference to the exemplary embodiments that are illustrated in the accompanying schematic figures, in which.

DETAILED DESCRIPTION

Figure 1:
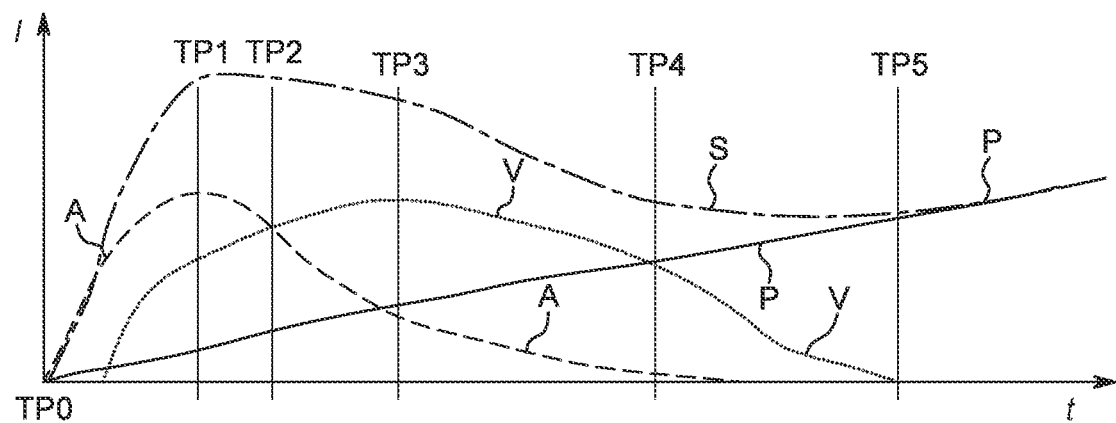
FIG. 1 is a graph of a temporal profile of concentrations of contrast agent in liver arteries (A), liver veins (V), and liver cells (P) and a summed enhancement (S) for a voxel which contains each of liver artery tissue, liver vein tissue, and liver cell tissue.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible.

As used herein, the term "computing device" may refer to one or more electronic devices that are configured to directly or indirectly communicate with or over one or more networks. A computing device may be a mobile or portable computing device, a desktop computer, a server, and/or the like. Furthermore, the term "computer" may refer to any computing device that includes the necessary components to receive, process, and output data, and normally includes a display, a processor, a memory, an input device, and a network interface. A "computing system" may include one or more computing devices or computers. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.). Further, multiple computers, e.g., servers, or other computerized devices, such as an autonomous vehicle including a vehicle computing system, directly or indirectly communicating in the network environment may constitute a "system" or a "computing system".

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Referring now to FIG. 1, FIG. 1 shows schematically the temporal profile of the concentrations of contrast agent in the liver arteries (A), the liver veins (V), the liver cells (P) and a summed enhancement (S) for a voxel which contains all three types of tissue (e.g., each of liver artery tissue, liver vein tissue, and liver cell tissue), and has already been described in detail herein above.

Figure 2:
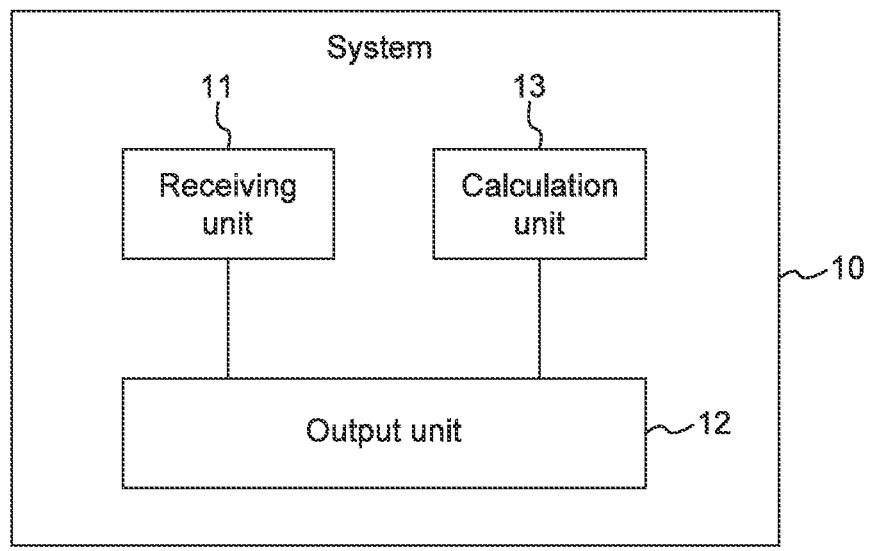
FIG. 2 is a diagram of a system according to non-limiting embodiments or aspects.

Referring also to FIG. 2, FIG. 2 shows schematically a system according to non-limiting embodiments or aspects. The system (10) comprises a receiving unit (11), a control and calculation unit (12) and an output unit (13).

Figure 3:
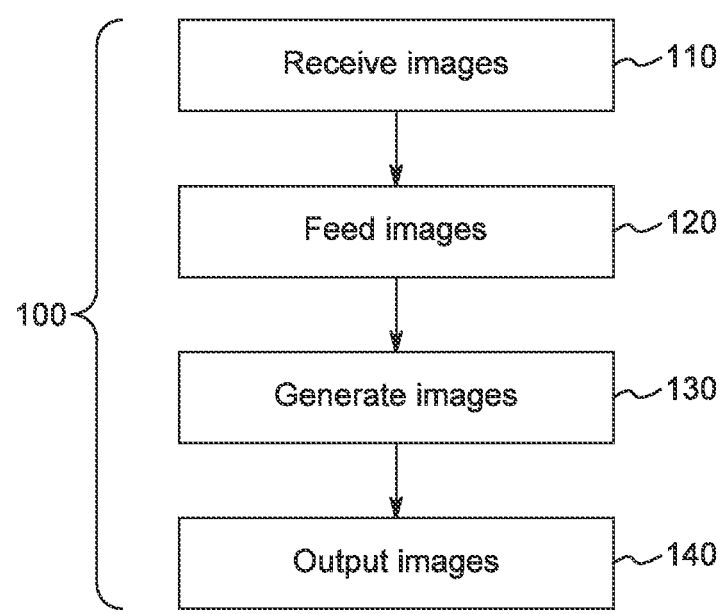
FIG. 3 is a flowchart of non-limiting embodiments or aspects of a process for predicting, anticipating, and/or assessing tissue characteristics.

Referring also to FIG. 3, FIG. 3 is a flowchart of a method according to non-limiting embodiments or aspects. The method (100) comprises the steps:

(110) receiving a plurality of MRI images, the MRI images showing an examination region during a first time span, (120) feeding the plurality of MRI images to a prediction model, the prediction model having been trained by means of supervised learning to predict, on the basis of MRI images showing an examination region during a first time span, one or more MRI images showing the examination region during a second time span, (130) generating one or more predicted MRI images showing the examination region during a second time span by means of the prediction model, (140) displaying and/or outputting the one or more predicted MRI images and/or storing the one or more predicted MRI images in a data storage medium.

Figure 4:
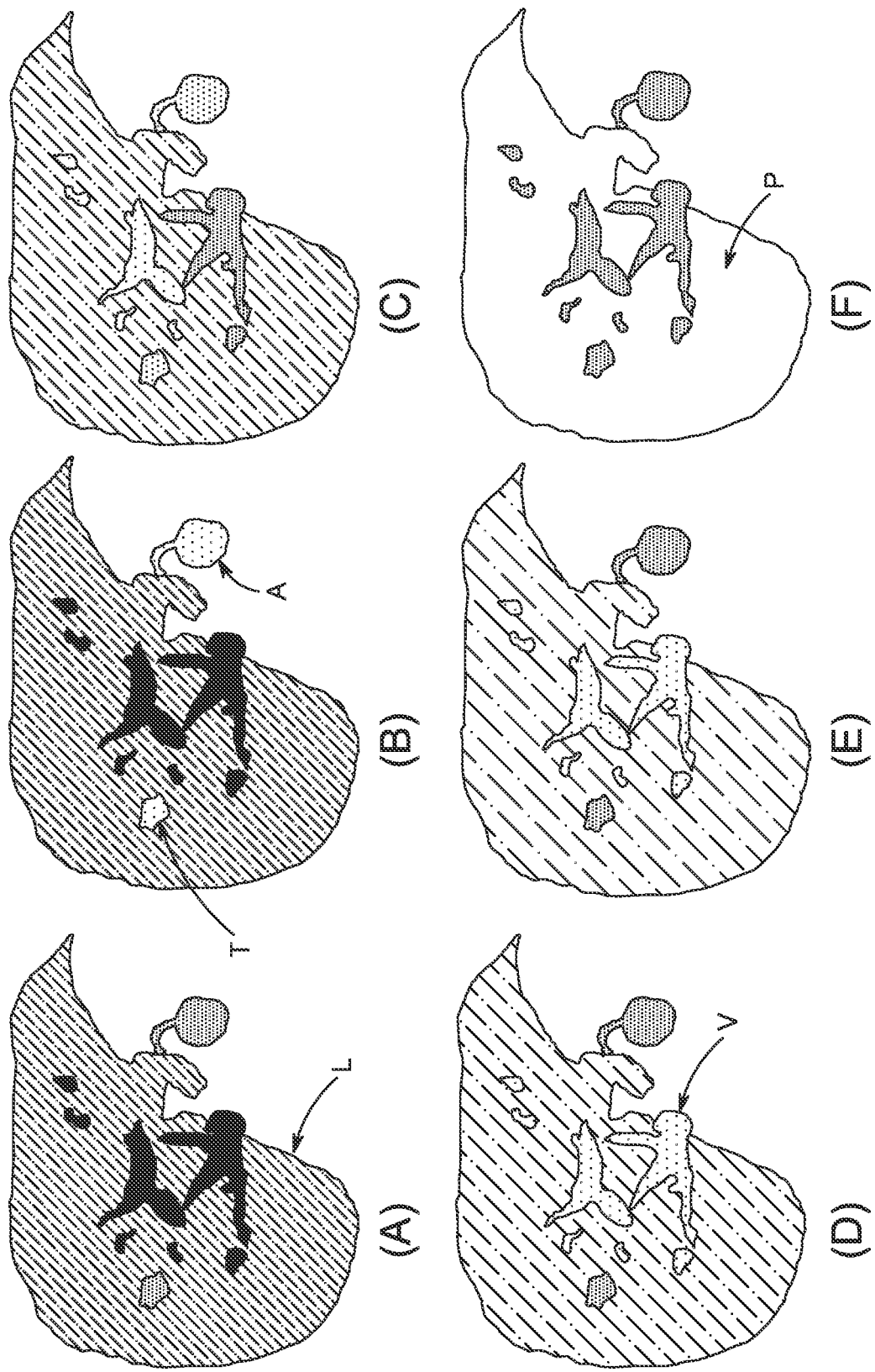
FIG. 4 shows MRI images of the liver during the dynamic and the hepatobiliary phase.

Referring also to FIG. 4, FIG. 4 shows MRI images of the liver during the dynamic and the hepatobiliary phase. In FIGS. 4(*a*), 4(*b*), 4(*c*), 4(*d*), 4(*e*) and 4(*f*), the same cross section through the liver at different time points is always depicted. The reference signs entered in FIGS. 4(*a*), 4(*b*), 4(*d*) and 4(*f*) apply to all of FIGS. 4(*a*), 4(*b*), 4(*c*), 4(*d*), 4(*e*) and 4(*f*); they are each entered only once merely for the sake of clarity.

FIG. 4(*a*) shows the cross section through the liver (L) before the intravenous administration of a hepatobiliary contrast agent. At a time point between the time points depicted by FIGS. 4(*a*) and 4(*b*), a hepatobiliary contrast agent was administered intravenously as a bolus. This reaches the liver via the liver artery (A) in FIG. 4(*b*). Accordingly, the liver artery is depicted with signal enhancement (arterial phase). A tumour (T), which is supplied with blood mainly via arteries, likewise stands out from the liver-cell tissue as a lighter (signal-enhanced) region. At the time point depicted in FIG. 4(*c*), the contrast agent reaches the liver via the veins. In FIG. 4(*d*), the venous blood vessels (V) stand out from the liver tissue as light (signal-enhanced) regions (venous phase). At the same time, the signal intensity in the healthy liver cells, which are supplied with contrast agent mainly via the veins, continuously rises (FIG. 4(*c*)→4(*d*)→4(*e*)→4(*f*)). In the hepatobiliary phase depicted in FIG. 4(*f*), the liver cells (P) are depicted with signal enhancement; the blood vessels and the tumour no longer have contrast agent and are accordingly depicted darkly.

Figure 5:
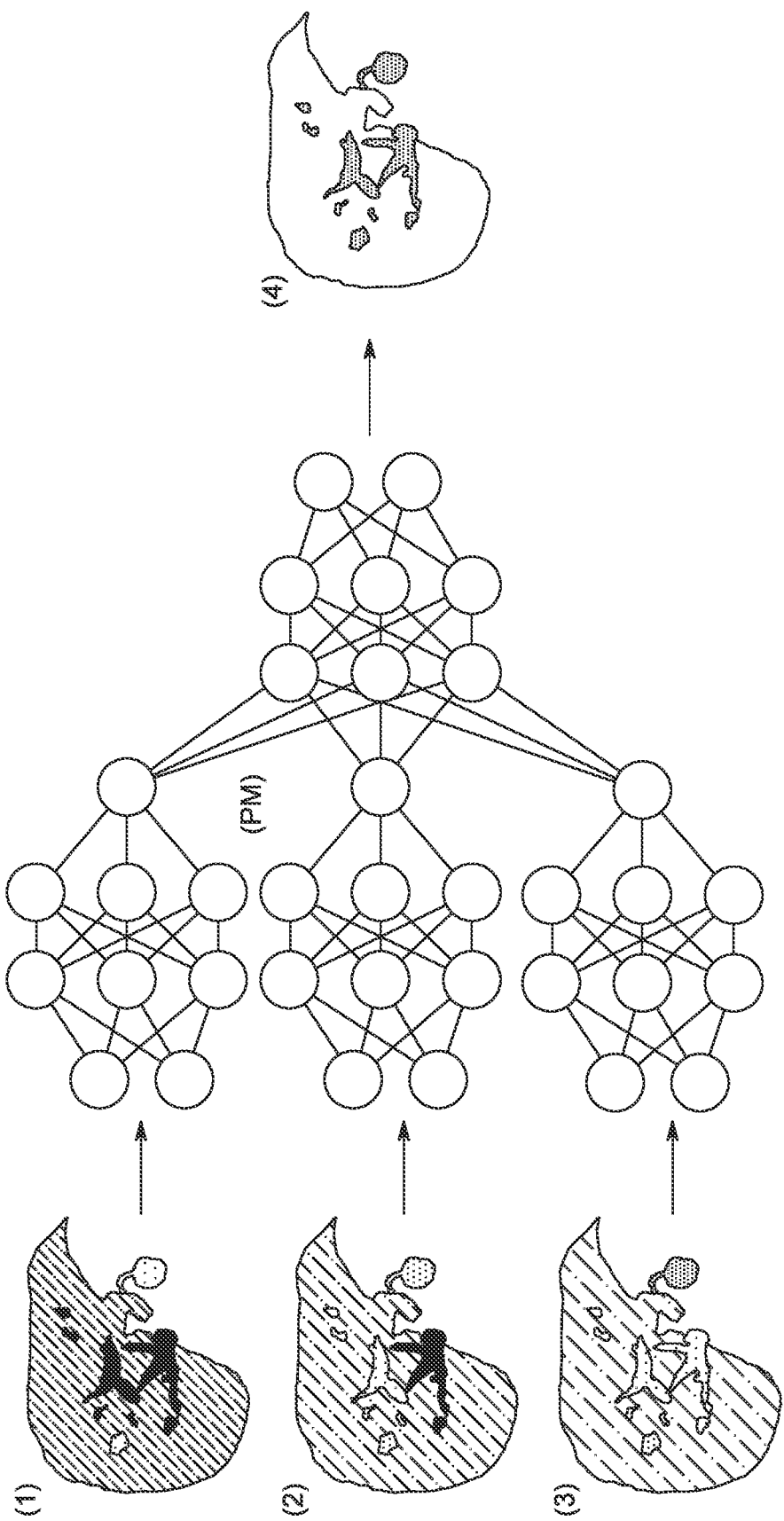
FIG. 5 shows three MRI images (1), (2) and (3) showing a liver in a first time span and an MRI image (4) showing the liver in a second time span.

Referring also to FIG. 5, FIG. 5 shows exemplarily and schematically how three MRI images (1), (2) and (3) showing a liver in a first time span are fed to a prediction model (PM). The prediction model calculates from the three MRI images (1), (2) and (3) an MRI image (4) showing the liver in a second time span. The MRI images (1), (2) and (3) can, for example, show the MRI images shown in FIGS. 4(*b*), 4(*c*) and 4(*d*), The MRI image (4) can, for example, be the MRI image shown in FIG. 4(*f*).

Medical needs unmet by existing imaging systems and/or image analysis systems include at least the following: identification and assessment of healthy tissue and/or different grades of pathological tissue, differentiation between different diseases and/or pathological stages, improved imaging/scan workflows, generation of cell specific and/or cell functional information, and function information on hollow or tubular organs or organ systems.

Non-limiting embodiments or aspects of the present disclosure provide for and/or improve at least the following: the identification and assessment of healthy tissue and/or different grades of pathological tissue (e.g., diffuse pathologies, such as tissue fibrosis/cirrhosis, inflammation, fatty infiltration, functional impairment/death, and/or the like, focal pathologies, such as benign or malignant tumours, and/or the like, etc.), the differentiation between different diseases and/or pathological stages (e.g., diffuse pathologies, focal pathologies, etc.), the imaging/scan workflow (e.g., faster image generation and/or acquisition, etc.), the generation of cell specific or cell functional information (e.g., cell function, such as cell ability and speed to uptake and excrete certain drugs or metabolites, and/or the like, molecular information, such as, the amount of cell oxygenation, the expression of certain cell antigens, channels/membrane proteins, and/or the like, etc.), and/or the function information on hollow or tubular organs or organ systems (e.g., vessel systems, biliary system, vascular pressure, such as portal venous system, etc.). Non-limiting embodiments or aspects of the present disclosure provide for voxel specific estimations of one or more of arterial circulation volume, portal venous volume, venous volume, extracellular volume, bile duct volume, normal hepatocyte volume, fatty cell volume, fibrosis volume, Kupffer cell volume, stem cell volume, other liver cell volume, and/or metastatic or other lesion or non-liver cell volumes.

Figure 6:
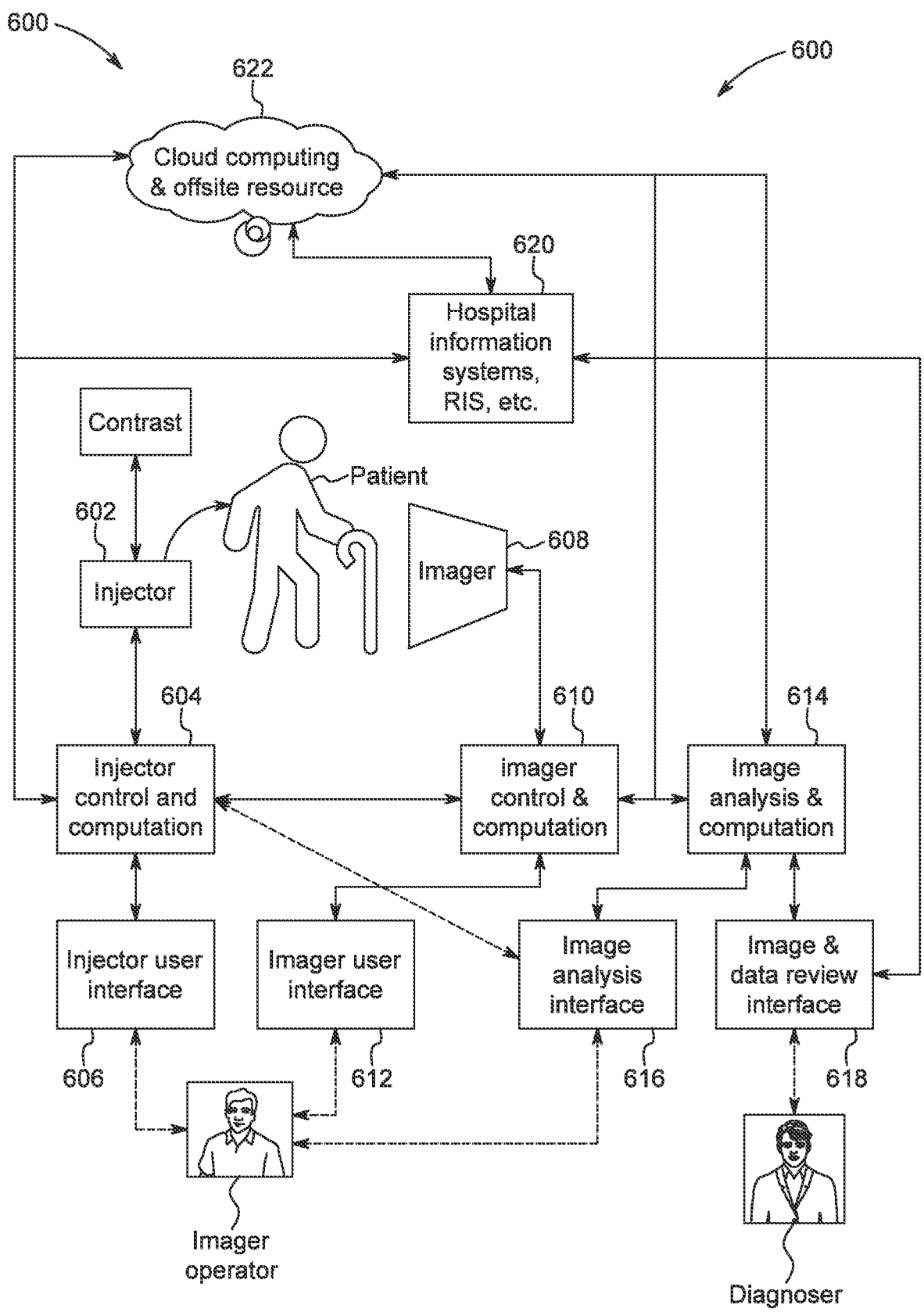
FIG. 6 is a diagram of non-limiting embodiments or aspects of an environment in which systems, devices, products, apparatus, and/or methods, described herein, can be implemented.

Referring now to FIG. 6, FIG. 6 is a diagram of an example environment 600 in which devices, systems, methods, and/or products described herein, may be implemented. As shown in FIG. 6, environment 600 includes contrast injector 602, injector control and computation system 604, injector user interface 606 imager 608, imager control and computation system 610, imager user interface 612, image analysis and computation system 614, image analysis interface 616, image and data review interface 618, hospital information system(s) 620, and/or cloud computing and offsite resources 622. Systems and/or devices of environment 600 can interconnect via wired connections, wireless connections, or a combination of wired and wireless connections. For example, systems and/or devices of environment 600 may interconnect (e.g., communicate information and/or data, etc.) via a cellular network (e.g., a long-term evolution (LTE) network, a third generation (3G) network, a fourth generation (4G) network, a fifth generation network (5G), a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, a short range wireless communication network, and/or the like, and/or any combination of these or other types of networks. Contrast injector 602, injector control and computation system 604, and/or injector user interface 606 may comprise a contrast injection system with respective software and/or hardware to set up one or more injection protocols and deliver one or more contrast agents to a patient according to the one or more injection protocols. In some non-limiting embodiments or aspects, contrast injector 602, injector control and computation system 604, and/or injector user interface 606 may include a contrast injection system as described in U.S. Pat. Nos. 6,643,537 and 7,937,134 and published International Application No. WO2019046299A1, the entire contents of each of which is hereby incorporated by reference. In some non-limiting embodiments or aspects, contrast injector 602, injector control and computation system 604, and/or injector user interface 606 may comprise the MEDRAD® Stellant FLEX CT Injection System, the MEDRAD® MRXperion MR Injection System, the MEDRAD® Mark 7 Arterion Injection System, the MEDRAD® Intego PET Infusion System, the MEDRAD® Spectris Solaris EP MR Injection System, the MEDRAD® Stellant CT Injection System With Certegra® Workstation, and/or the like.

Imager 608, imager control and computation system 610, and/or imager user interface 612 may comprise an imaging system with respective software and/or hardware to set up imaging protocols and acquire non-contrast and contrast-enhanced scans of a patient. In some non-limiting embodiments or aspects, imager 608, imager control and computation system 610, and/or imager user interface 612 may include an MRI system (e.g., MRI based on T1, T2, TWI, PD, mapping (fat, iron), a multiparametric approach, hyperpolarized MRI, MR Fingerprinting, elastography, etc.), a computed tomography (CT) system, an ultrasound system, a single-photon emission computed tomography (SPECT) system, a positron emission tomography—magnetic resonance (PET/MRI) system, a positron emission tomography—computed tomography (PET/CT) system, and/or other diagnostic imaging system. In some non-limiting embodiments or aspects, imager 608, imager control and computation system 610, and/or imager user interface 612 may include an imaging system as described in U.S. patent application Ser. No. 16/710,118, filed on Dec. 11, 2019, the entire contents of which is hereby incorporated by reference. In some non-limiting embodiments or aspects, imager 608, imager control and computation system 610, and/or imager user interface 612 may include Siemens Healthineers' Somatom Go CT systems, General Electric's Signa MR systems, and/or the like.

In some non-limiting embodiments or aspects, one or more of contrast injector 602, injector control and computation system 604, injector user interface 606, imager 608, imager control and computation system 610, imager user interface 612, image analysis and computation system 614, image analysis interface 616, image and data review interface 618, hospital information system(s) 620, and/or cloud computing and offsite resources 622 may include a computer system as described herein and/or one or more components and/or peripherals of a computer system.

A patient may include a living organism (e.g., a mammal, a human, etc.) including multiple tissues and/or organs with different types of cells (e.g. a liver including hepatocytes, Kupffer cells, immune-cells, stem-cells, etc.), afferent and/or efferent supply/circulation systems (e.g., arteries, veins, a lymphatic or biliary system, etc.), and/or different compartments/spaces (e.g., vascular space, interstitial space, intracellular space, etc.).

A contrast agent delivered to a patient by a contrast injection system may be selected or configured according to a type of the imaging system used to scan the patient. A contrast agent may include gadolinium-based contrast agents (GBCA) (e.g., for use in MRI, etc.), iodine based contrast agents (e.g., for use in CT, etc.) an ultrasound contrast media (e.g., microbubbles, etc.), and/or other more uncommon contrast agents, such as iron-based agents (e.g., small, or ultra-small superparamagnetic iron oxide, manganese-based, $CO_2$, or other agents), blood pool agents (e.g., having an intravascular long blood half-life), agents with kidney dominant or hepatobiliary dominant excretion, agents with intracellular uptake, and organ-specific or cell-specific uptake, agents with organ- or cell specific binding (e.g., without intracellular uptake), agents with long "retention" (e.g. FDG), and/or the like. A contrast agent may be radioactive. A contrast agent may be cell marker specific, meaning that it bonds or interacts with certain cell surface or cell interior markers. The contrast agent involved may be a native contrast, for example oxygen levels in haemoglobin. A contrast agent maybe a negative contrast, for example which reduces the haematocrit and, thus, the red blood cell signal in the blood or microbubbles, which replaces the blood with a gas. In normal MRI, the gas gives no signal and in CT the gas produces increased transmission and thus reduced Hounsfield units.

A contrast injection system may deliver a single agent (e.g., a single contrast agent delivered by itself, etc.) or multiple contrast agents in combination at the same time (e.g., multiple parallel injections, an injection of two fluids mixed together, or one after the other (e.g., multiple consecutive injections)). An imaging system can perform a single image acquisition or scan at one or more time points (phases), multiple acquisitions at one or more time points (e.g, using MR-mapping techniques, etc.), and/or an acquisition across continuous imaging periods.

In some non-limiting embodiments or aspects, a contrast injection may be delivered to one or more different locations or compartments, such as a venous vascular compartment, an arterial vascular compartment, a lymphatic vascular compartment, and/or the like.

Figure 7:
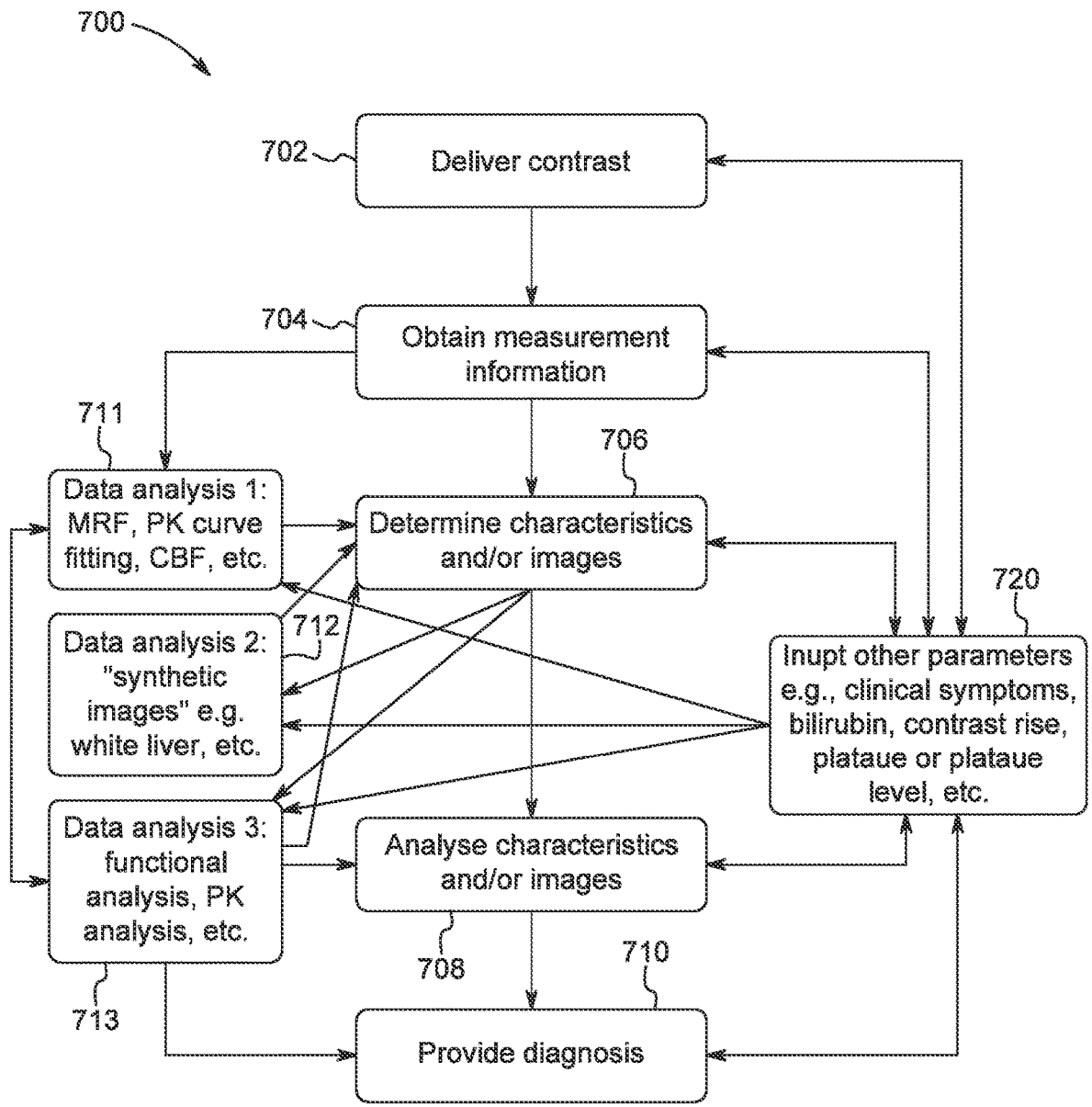
FIG. 7 is a flowchart of non-limiting embodiments or aspects of a process for predicting, anticipating, and/or assessing tissue characteristics.

Referring now to FIG. 7, FIG. 7 is a flowchart of non-limiting embodiments or aspects of a process 700 for predicting, anticipating, and/or assessing tissue characteristics. In some non-limiting embodiments or aspects, one or more of the steps of process 700 may be performed (e.g., completely, partially, etc.) by image analysis and computation system 614 (e.g., one or more devices of image analysis and computation system 614). In some non-limiting embodiments or aspects, one or more of the steps of process 700 may be performed (e.g., completely, partially, etc.) by another device or a group of devices separate from or including image analysis and computation system 614, such as imager control and computation system 610 (e.g., one or more devices of imager control and computation system 610), hospital information system(s) 620 (e.g., one or more devices of hospital information system(s)), cloud computing and offsite resources system 622 (e.g., one or more devices of cloud computing and offsite resources system 622), and/or the like.

As shown in FIG. 7, at step 702 process 700 includes delivering contrast agent to a patient. For example, a contrast injection system may deliver (e.g., inject, etc.) contrast agent to a patient. As an example, contrast injector 602, injector control and computation system 604, and/or injector user interface 606 may set up one or more injection protocols and deliver one or more contrast agents to a patient according to the one or more injection protocols.

In some non-limiting embodiments or aspects, contrast agent may be delivered to a patient in a compact, short and relatively quick bolus to allow individual phases (e.g., an arterial phase, a portal-venous phase, a venous phase, etc.) to be distinguished. For example, contrast concentration may be relatively homogenous during a short period of "steady state" before contrast distributes through the body to allow for a short phase of steady state imaging. In some non-limiting embodiments or aspects, contrast agent may be delivered to a patient to slow down or stretch the injection time of the contrast agent as described in U.S. Pat. No. 9,436,989, the entire contents of which is hereby incorporated by reference. In some non-limiting embodiments or aspects, contrast agent may be delivered to a patient to achieve a desired MR contrast concentration in blood and/or in tissue such that an MR fingerprint can include one or more contrast related parameters as described in U.S. patent application Ser. No. 16/462,410, filed on Nov. 21, 2017, the entire contents of which is hereby incorporated by reference. In some non-limiting embodiments or aspects, an injection speed/delivery of a contrast agent may be performed as a single fast bolus (e.g., to distinguish phases), as a single bolus to enable imaging in real time from time X to time Y, as two discrete image periods (e.g., 0.5 to 2 min and then 10 or 20 min, etc.), as a single slow bolus (e.g., with normal phases not visibly distinguishable, etc.), or as a dual bolus (e.g., in a sequence including delivery of a first bolus, waiting, imaging, delivery of a second bolus, and imaging, etc.).

As shown in FIG. 7, at step 704, process 700 includes obtaining measurement information associated with tissue of a patient. For example, an imaging system may set up one or more imaging protocols and acquire non-contrast and/or contrast-enhanced scans of tissue of the patient to obtain measurement information associated with the tissue of the patient (e.g., one or more images or scan of the tissue of the patient, etc.) according to the one or more imaging protocols. As an example, imager 608, imager control and computation system 610, and/or imager user interface 612 (and/or image analysis and computation system 614) may obtain measurement information associated with a parameter of a voxel of tissue of the patient measured at two or more time points (e.g., values of the parameter of the voxel of the tissue at the two or more time points, images or scans of the tissue including or showing the parameter at the two or more time points, etc.). In some non-limiting embodiments or aspects, the two or more time points occur before one or more characteristics of the voxel of tissue are separable (e.g., separable from one or more other characteristics and/or noise in the measurement data and/or an image created from the measurement data, etc.) and/or discernible (e.g., discernible by a human eye, etc.) in an image generated based on the parameter of the voxel at a single time point of the two or more time points.

In some non-limiting embodiments or aspects, measurement information may be obtained (e.g., scanned, imaged, etc.) at different (e.g., discrete) times or continuously before, during, and/or after contrast injection resulting in one or more of the following parameter/image acquisition phases: a native phase (e.g., before contrast), an arterial phase, a portal venous phase, a venous phase, an equilibrium phase, in a case of hepatobiliary uptake and excretion: a hepatobiliary phase (HBP), and/or as a continuous image acquisition over one or more phases.

In some non-limiting embodiments or aspects, image acquisition or scanning to obtain measurement data may be started at a time point (e.g., an optimal time point, etc.) determined based on a circulation time of a patient as described in EP Patent Application No. 20161359.3, the entire contents of which hereby incorporated by reference.

In some non-limiting embodiments or aspects, measurement information including one or more parameters of a voxel of tissue may be obtained using at least one of the following techniques: an MRI acquisition technique (e.g., MRI based on T1, T2, TWI, PD, mapping (fat, iron), a multiparametric approach, hyperpolarized MRI, MR Fingerprinting, elastography, etc.), a CT acquisition technique, an ultrasound technique, a SPECT technique, a PET/MRI technique, a PET/CT technique, another diagnostic imaging technique, or any combination thereof.

In some non-limiting embodiments or aspects, a parameter of a voxel of tissue measured by an imaging system may include at least one of the following: T1 weighted (T1w), T2 weighted (T2w), proton density weighted (PDw), diffusion weighted (DWI), x-ray absorption amount, a shortening amount of T1 and/or T2 relaxation times, a change in x-ray absorption amount, a tracer uptake amount/a metabolism and registration of emissions, one or more pharmacokinetic model parameters, or any combination thereof. For example, an image acquired by an imaging system may include or show the parameter of the voxel of the tissue at the time the parameter is measured by the imaging system.

As shown in FIG. 7, at step 706, process 700 includes determining one or more characteristics associated with tissue of a patient. For example, image analysis and computation system 614 may determine, based on the parameter of the voxel at the two or more time points, the one or more characteristics. As an example, image analysis and computation system 614 may generate, based on the measurement information including the one or more parameters of the voxel at the two or more time points (and/or images including or showing the parameter of the voxel at the two or more time points), one or more images including or showing the one or more characteristics of the voxel of the tissue of the patient. In such an example, image analysis and computation system 614 may synthesize, enhance, combine, and/or replace/eliminate one or more images acquired and/or not acquired by the imaging system that acquired or measured the measurement information including the parameter of the voxel at the two or more time points. For example, a single characteristic may be displayed as a gray scale image. As another example, two or more characteristics may be displayed as a color overlay on a gray scale image.

In some non-limiting embodiments or aspects, the one or more characteristics (and/or the one or more images including or showing the one or more characteristics) may be determined for a time point and/or a time period corresponding to (e.g., at the same time as, etc.) one or more of the two or more time points. In some non-limiting embodiments or aspects, the one or more characteristics (and/or the one or more images including or showing the one or more characteristics) may be determined for a time point and/or a time period after the two or more time points (e.g., subsequent to the two or more time points, etc.).

In some non-limiting embodiments or aspects, a characteristic associated with tissue of a patient may include at least one of the following: a concentration of contrast agent in arteries of a voxel (e.g., in liver arteries (A), etc.), a concentration of contrast agent in veins of a voxel (e.g., in liver veins (V), etc.), a concentration of contrast agent in cells of a voxel (e.g., in liver cells (P), etc.), a summed enhancement of the concentration of contrast agent in the arteries, veins, and cells of a voxel (e.g., a summed enhancement of the concentration of contrast agent in the liver arteries (A), the liver veins (V), the liver cells (P) of a voxel of liver tissue, etc.), one or more of the pharmacokinetic parameters associated with contrast movement through the tissue spaces of a voxel, or any combination thereof. In some non-limiting embodiments or aspects, a characteristic associated with tissue of a patient may include at least one characteristic not associated with the injected contrast including, for example, electron density, hydrogen density, T1, T2, apparent diffusion coefficient (ADC), or any combination thereof.

In the earliest days of medical imaging, the acquisition of data and creation of image(s) was performed by having X-rays traverse the patient and be absorbed by a light emitting screen paired with photographic film which was developed to create the image. That film was then read by the radiologist who made the diagnosis. With current electronic and computer technology, there are multiple imaging modalities with different ways of acquiring 2D or 3D arrays of data (over time (4D) and translating this data into images, meaning 2D, 3D, or 4D human understandable representations of the data. One can also speak of a $5^{th}$ dimension, which is the ability to collect multiple parameters of data at each point in time for each voxel in the patient region of interest. As further shown in FIG. 7, example but non-limiting data analysis steps may include data analysis 711 which, for example turns the acquired data or images into human readable images, data analysis 712 which, for example uses two or more images to create a previously non-existing image in human readable form, data analysis 713 which, for example may inform the reader or recommend or make a diagnosis for confirmation by the medical professional involved. Computer aided diagnosis algorithms are an example of this data analysis. For example, image analysis and computation system 614 may determine, based on the measurement information including the parameter of the voxel at the two or more time points, the one or more characteristics (and/or the one or more images including or showing the one or more characteristics, and/or diagnosis information associated therewith) using at least one of the following techniques: a window & level technique, a gamma correction technique, a filtered back projection technique, an iterative reconstructions technique, a model fitting technique, a dictionary mode of curve fitting technique (e.g., MR-fingerprinting, etc.), a spatial, temporal filtering and enhancement technique, a feature extraction technique using CAD or AI, a fractal analysis technique, a motion correction technique, a flexible registration technique, a parameter quantification technique, 2D AI or machine learning based analysis of a single image, a 2D AI or machine learning based analysis technique of time sequence for a voxel, a 3D AI or machine learning based analysis technique of a time sequence of images technique, an AI or machine learning based denoising or sharpening technique, an AI or machine learning based contrast amplification technique, or any combination thereof.

In some non-limiting embodiments or aspects, image analysis and computation system 614 (and/or imager control and computation system 610) may determine that the measurement information associated with the parameter of the voxel of the tissue of the patient includes a threshold amount of measurement information associated with determining the one or more characteristics of the voxel of the tissue (e.g., a sufficient amount of information and/or data to determine the one or more characteristics and/or the one or more images including the one or more characteristics, etc.) and, in response to determining that the measurement information includes the threshold amount of measurement information, control an imaging system (e.g., imager 608, etc.) to automatically stop acquisition of the measurement information (e.g., to stop scanning or imaging the patient, etc.). In some non-limiting embodiments or aspects, the threshold amount of measurement information associated with determining the one or more characteristics of the voxel of the tissue may include a threshold amount of information associated with providing one or more selected or predetermined diagnoses for the patient, optionally with a predetermined level of parameter differentiation, confidence of prediction, or margin of error.

Figure 9:
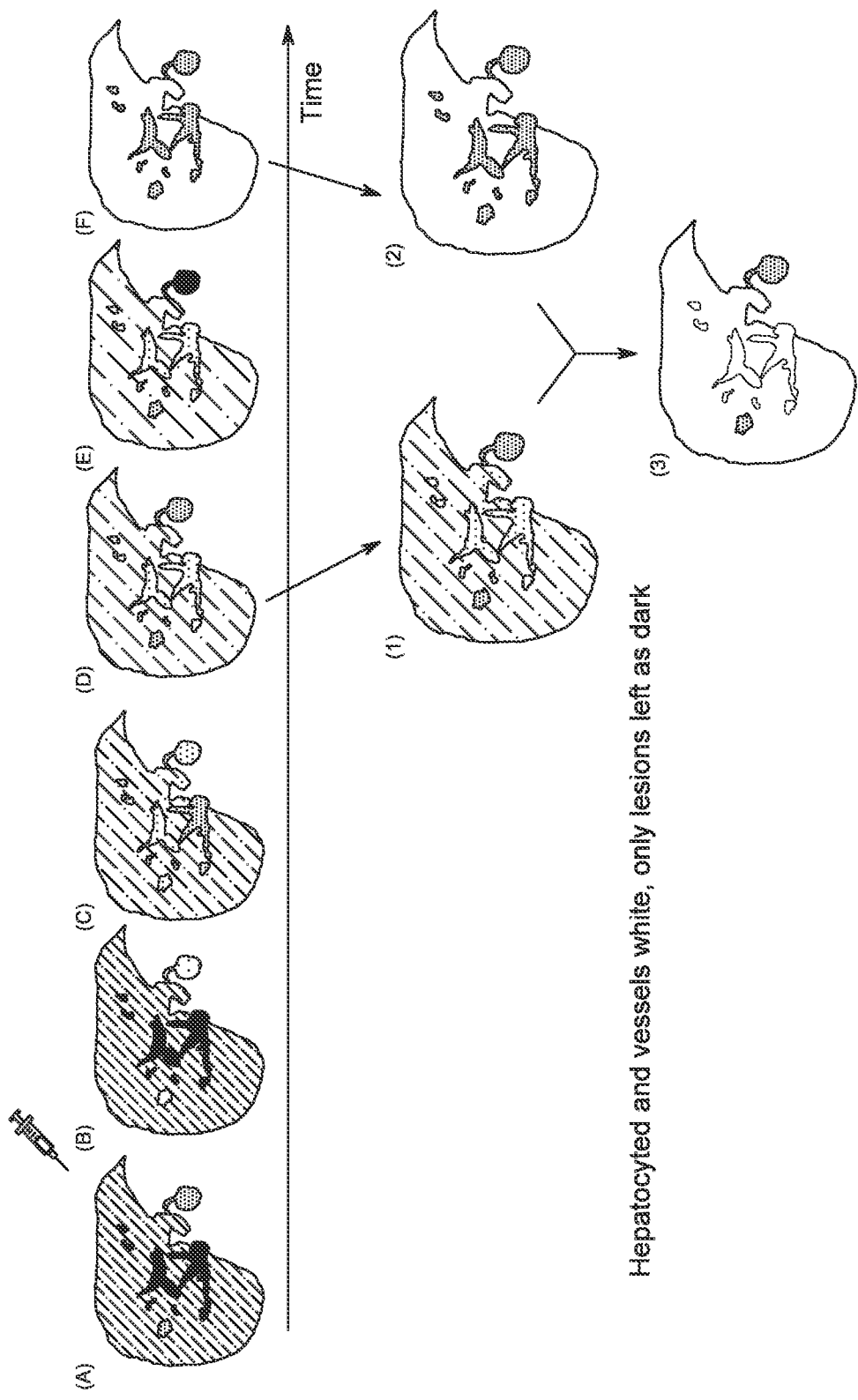
FIG. 9 shows an MRI images (3) synthesized by combining contrast information known from the HBP for liver specific contrast agents with MRI images (1), (2) of earlier phases of the liver to generate a "plain-white-liver" image.
Figure 10:
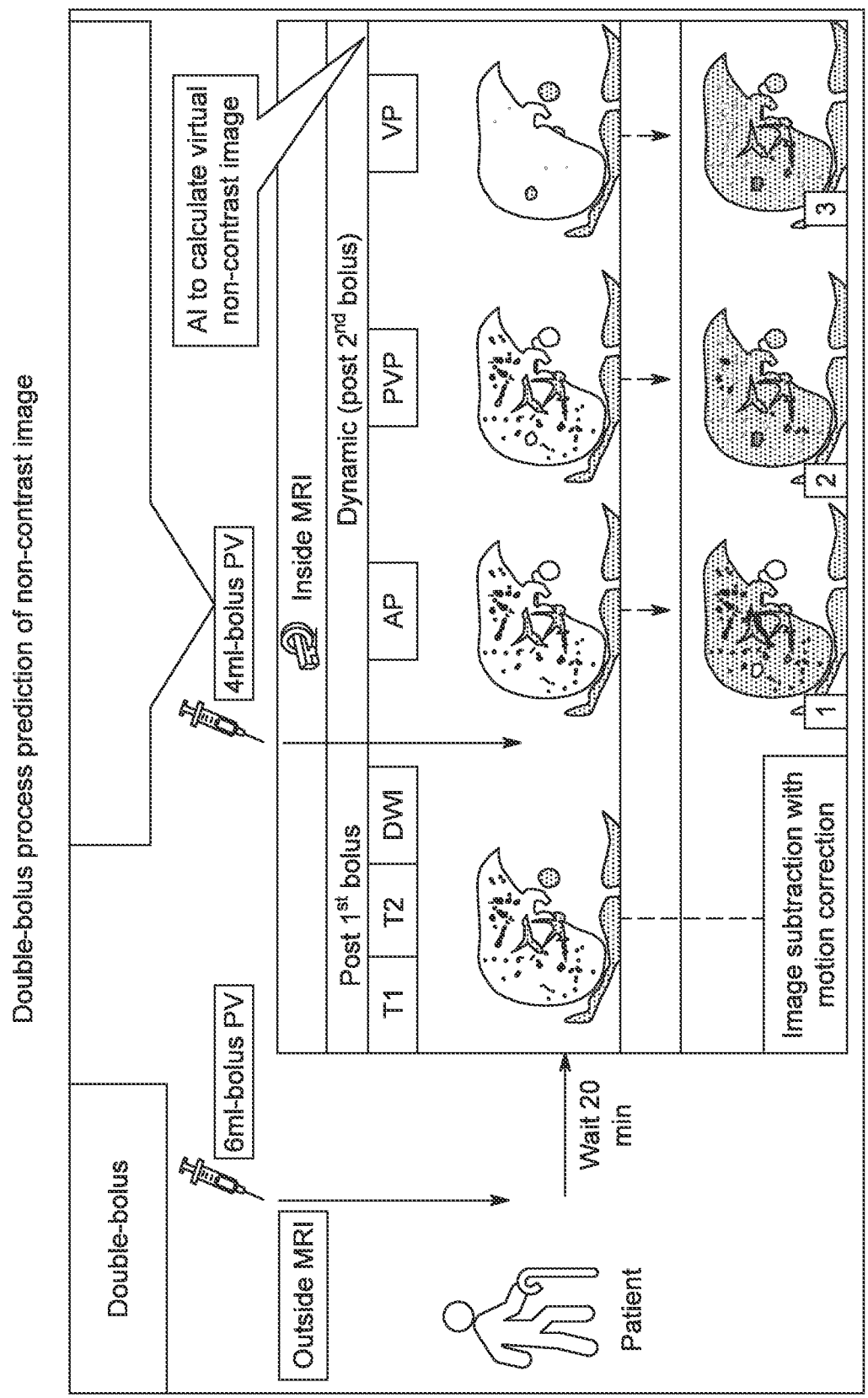
FIG. 10 shows non-enhanced Tlw images (1), (2), (3) synthesized from measured contrast enhanced images.

In some non-limiting embodiments or aspects, image analysis and computation system 614 may synthesize one or more images (e.g. generate or create one or more composite or enhanced images, one or more non-enhanced/contrast-enhanced/tracer images, one or more T1w/T2w/PDw images (and/or variants of those, e.g., with/without fat-sat., with inversion pulses, etc.), one or more images of the arterial/portal venous/venous/equilibrium/HB phases, one or more images of MRI continuous acquisitions, one or more non-enhanced/contrast-enhanced/tracer x-ray absorption images, one or more arterial/portal venous/venous/equilibrium/or continuous acquisition x-ray absorption images, etc.) of the voxel of the tissue of the patient based on the measurement information including the parameter of the voxel at the two or more time points (and/or the one or more images including or showing the parameter of the voxel at the two or more time points). As an example, image analysis and computation system 614 may synthesize one or more images in the HBP from the measurement information including the parameter of the voxel at the two or more time points measured in one or more phases that occur before the HBP. As an example, image analysis and computation system 614 may synthesize one or more images by combining (e.g., adding, subtracting, multiplying, etc.) contrast information known from the HBP for liver specific contrast agents with one or more images of earlier phases of the liver (e.g. one or more images measured or acquired in the arterial, portal-venous, and/or venous phase, etc.) to generate a "plain-white-liver" as shown in FIG. 9 and described in further detail in EP Patent Application No. 19197986.3, filed on Sep. 18, 2019, and International Patent Application No. PCT/EP2020/075288, filed on Sep. 10, 2020, the entire contents of each of which is hereby incorporated by reference, which may include the combination of the entire information from two or multiple images or only part of the information from two or multiple images into a new synthesized image. As an example, image analysis and computation system 614 may synthesize non-enhanced T1w images from one or more measured contrast enhanced images (e.g. in the liver, etc.) as shown in FIG. 10 and described in further detail in EP Patent Application No. 19201919.8, filed on Oct. 8, 2019, the entire contents of which is hereby incorporated by reference. As an example, image analysis and computation system 614 may enhance certain image contrasts (e.g., contrast of the arterial phase enhancement in a contrast-enhanced T1w MR-image to enable high-contrast, high-accuracy imaging of tissues and tumours with reduced amounts of contrast agent, etc. as described in EP Patent Application No. 19201937.0, filed on Oct. 8, 2019, and U.S. Provisional Patent Application No. 62/943,980, filed on Dec. 5, 2019, the entire contents of each of which is hereby incorporated by reference. As an example, image analysis and computation system 614 may synthesize contrast-enhanced T1w images of the equilibrium phase (e.g., virtual blood-pool contrast images, etc.) as described in EP Patent Application No. 20167879.4, filed on Apr. 3, 2020, the entire contents of which is hereby incorporated by reference. As an example, image analysis and computation system 614 may synthesize images without gadoxetic acid-induced contrast changes within hepatocytes during the transitional phase or later phases from conventional gadoxetic-acid enhanced images. As an example, image analysis and computation system 614 may synthesize "pseudo images" based on a set of conventionally acquired mapping sequences that contain information on the full relaxation curve of a tissue over a pharmacokinetic time-frame while a substance (e.g. contrast agent) is passing through the tissue.

Figure 11:
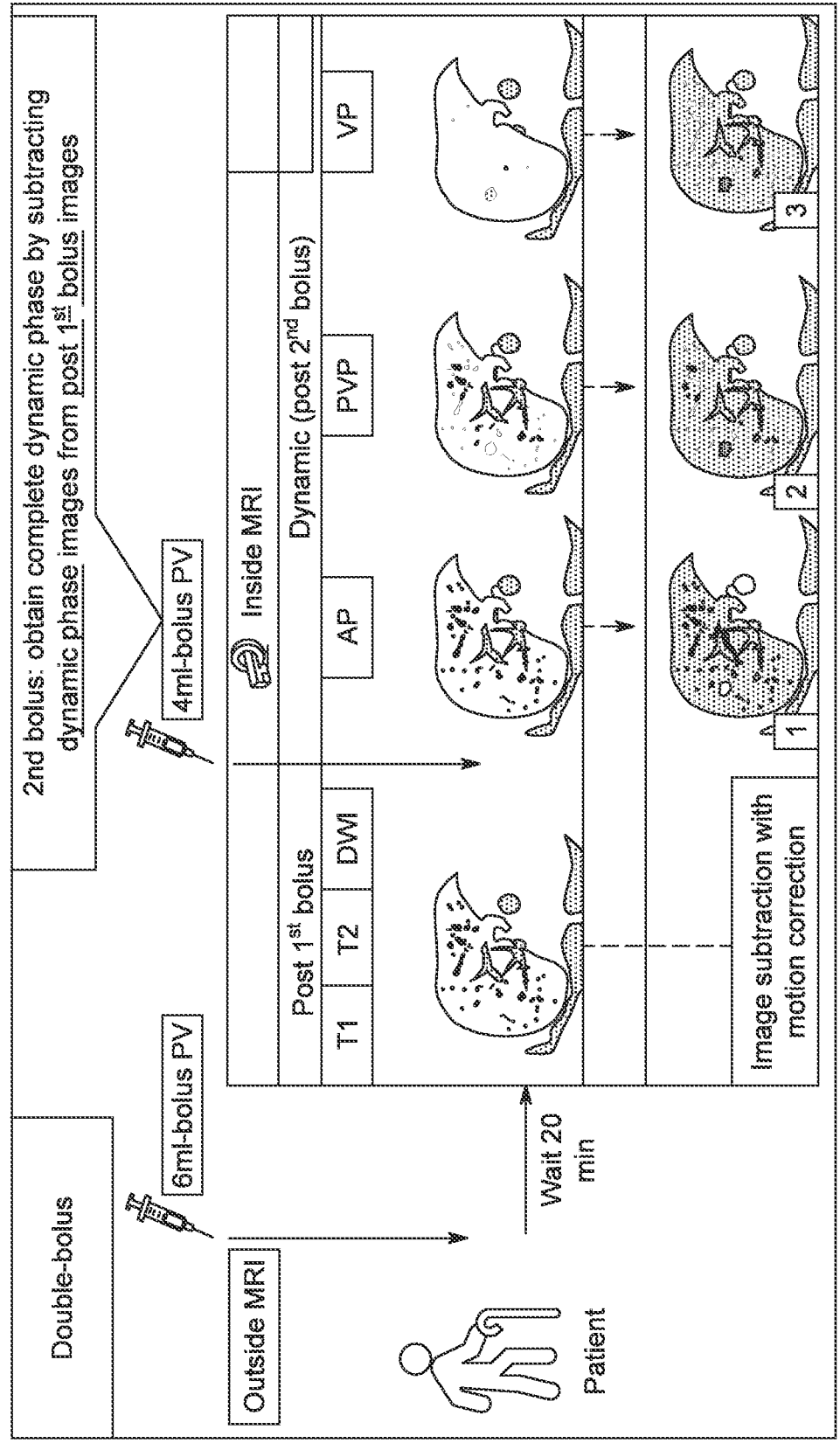
FIG. 11 shows images which show a blood vessel enhancement separate from an equilibrium uptake derived by subtracting one or more post equilibrium update images from one or more post second injection images.

As an example, a double injection protocol of contrast may be used, as shown in FIG. 11 and described in further detail in EP Patent Application No. 19201919.8, filed on Oct. 8, 2019, EP Patent Application No. 19202711.8, filed on Oct. 11, 2019, and EP Patent Application No. 20173089.2, filed on May 6, 2020, the entire contents of each of which is hereby incorporated by reference. A first injection of the double injection may be performed while the patient is not in the scanner. The first injection may, for example, be gadoxetic acid if the study is to be an MRI study. The patient remains out of the scanner while the contrast equilibrates in the body and is taken up by the target tissues. The patient is placed in the scanner and one or more images may be taken of that equilibrium uptake, as well as images that are not affected by the uptake. A second contrast injection of the double injection is then given, and one or more additional images are taken. These post second injection images may be timed to enable visualization and/or measurement of blood vessel enhancement, e.g., in addition to the equilibrium uptake imaging. As an example, image analysis and computation system 614 may subtract one or more post equilibrium update images from the one or more post second injection images to derive images which show the blood vessel enhancement separate from the equilibrium uptake at the corresponding points in time. The second contrast injection may be the same type of contrast as the first, or because the uptake has already occurred and has been imaged, it may be a different type of contrast, for example gadobutrol which has different and, in some ways, advantageous properties to gadoxetic acid. In some non-limiting embodiments or aspects, two different contrasts may be mixed or injected simultaneously. For example, a contrast agent with properties that make it preferable as a vascular contrast may be mixed with a contrast agent that is not as useful as a vascular phase contrast but has properties as a cell or tissue specific marker or contrast.

As shown in FIG. 7, at step 708, process 700 includes analysing one or more characteristics associated with tissue of a patient. In some non-limiting embodiments or aspects, a radiologist and/or other trained professional may read the one or more images including the one or more characteristics associated with the tissue of the patient to derive diagnosis information from the one or more images. In some non-limiting embodiments or aspects, image analysis and computation system 614 may analyse the one or more characteristics associated with the voxel of the tissue of the patient and/or the one or more images the one or more characteristics associated with the tissue of the patient to derive diagnosis information from the one or more images. For example, image analysis and computation system 614 may feed the one more characteristics (and/or the one or more images including or showing the one or more characteristics), to a classification model, the classification model having been trained by means of supervised learning to classify, on the basis of the one more characteristics (and/or the one or more images including or showing the one or more characteristics, the tissue as associated with one or more diagnoses. As an example, image analysis and computation system 614 may determine one or more diagnoses for the tissue using one or more of the techniques described herein above with respect to step 706 used to determine the one or more characteristics of the tissue.

In some non-limiting embodiments or aspects, diagnosis information may include an identification of a state (e.g., healthy tissue, non-healthy tissue, a type of non-healthy tissue, a type of illness associated with the tissue, etc.) of the voxel of the tissue of the patient, one or more reasons for the identification of the state of the voxel of the tissue of the patient, or any combination thereof.

As shown in FIG. 7, at step 710, process 700 includes providing a diagnosis associated with tissue of a patient. For example, a radiologist and/or other trained professional may provide the diagnosis information associated with the tissue of the patient. As an example, image analysis and computation system 614 may provide the diagnosis information associated with the tissue of the patient.

Still referring to FIG. 7, in some non-limiting embodiments or aspects, at step 720, additional information about the patient and/or a condition of the patient may be input and used at one or more of stages 702-710 to focus or affect selection among options at each stage and/or the determination of the information and/or data determined and/or generated at each stage. For example, the additional information about the patient and/or the condition of the patient may be input to a process, an algorithm, a machine learning model or neural network, a model fitting analysis, and/or the like used to determine the injection protocol, the imaging protocol, the measurement information, the one or more characteristics (and/or the one or more images including or showing the one or more characteristics), the diagnosis information, and/or the diagnosis. As an example, additional information associated with the patient and/or a condition of the patient, and/or desired conditions for the study may include at least one of the following: a height of the patient, a weight of the patient, an age of the patient, a gender of the patient, a heart rate of the patient, a cardiac output of the patient, a clinical symptom of the patient, a bilirubin level of the patient, a desired rate, rise and/or plateau level of the concentration of the contrast delivered to the patient, or any combination thereof. Additional examples of patient specific data may be found in U.S. Pat. Nos. 5,840,026 and 9,616,166, the contents of each of which is hereby incorporated by reference.

The data analysis steps 711, 712, 713 and associated computer hardware and/or software, for example image analysis and computation system 614, may also access and use the additional data 720 about the patient which, for example, may be obtained from the hospital information system 620 and/or other cloud computing data stores 622.

Figure 8:
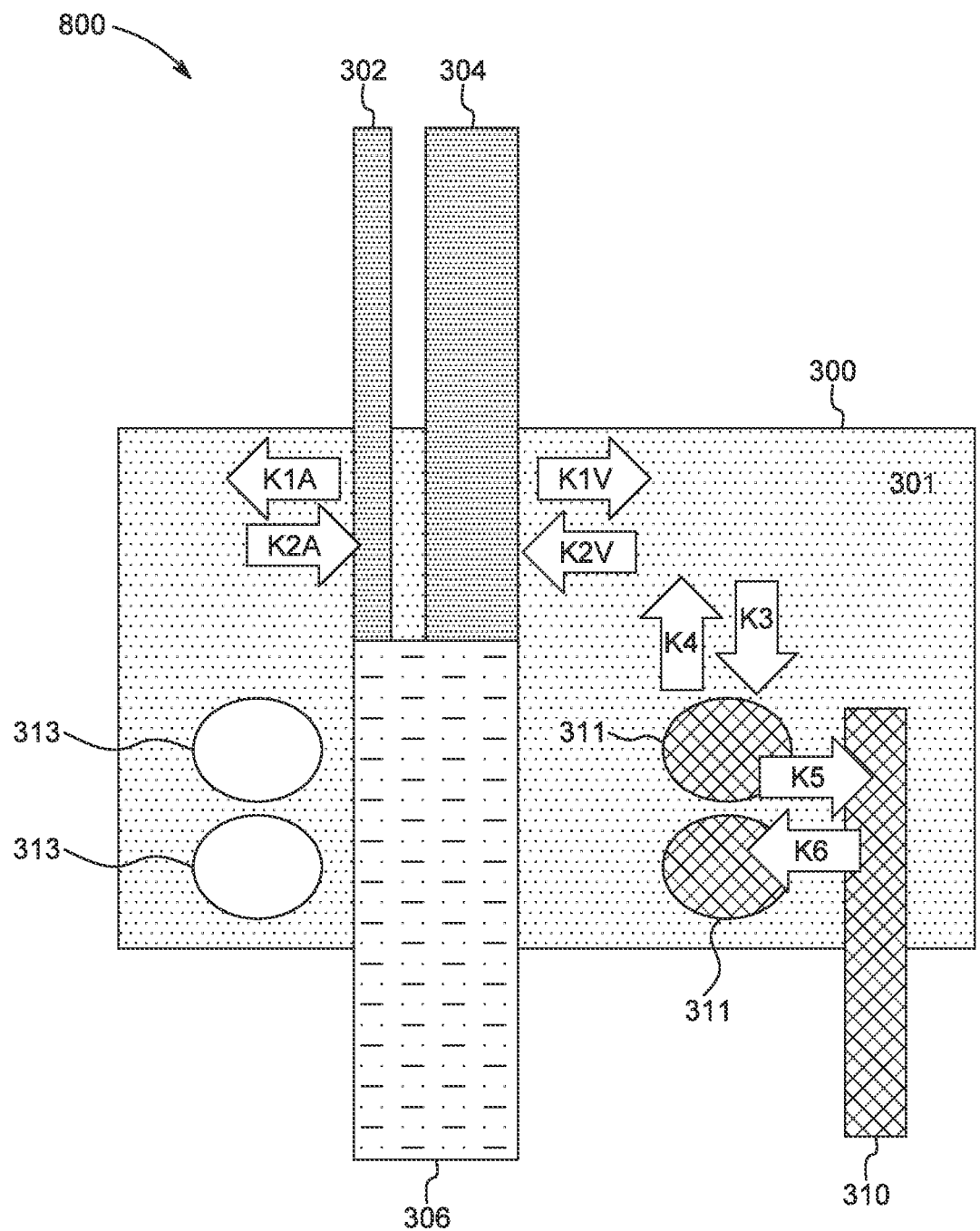
FIG. 8 is a non-limiting example of a pharmacokinetic model of liver tissue.

Referring now to FIG. 8, FIG. 8 shows a simplified schematic of a voxel 800 (e.g., a volume element, etc.) of an organ of a patient being imaged. This schematic is representative of the liver, but applies in general to other organs with appropriate adaptations or simplifications. The liver is a relatively complicated organ as is well known in medicine and physiology.

Each of the example elements may occupy some fractional volume of the voxel. The liver receives a dual blood supply from the hepatic portal vein 304 and hepatic arteries 302. The hepatic portal vein 304 delivers around 75% of the liver's blood supply and carries venous blood drained from the spleen, gastrointestinal tract, and its associated organs. The hepatic veins 306 carry the blood back to the heart. In each voxel there are cells. Some cells 311 may process or take up the contrast being used in imaging. These cells 311 may move the contrast into the bile ducts 310. The voxel may contain other cells 313 which effectively do not take up the contrast. There is also extracellular space 301 which represents the fluid and connective molecules that hold all these other components in place. Of course, in some parts of an organ, there may be voxels which are fully within one type of components, for example an artery, a vein, or a bile duct. Other voxels will have other fractions of the voxel elements.

Molecules may move from the blood into the extracellular volume and thence into the cells or bile ducts and vice versa. Different molecules diffuse or are transported at different rates depending upon their characteristics and the characteristics of the structures or cells involved. PK/PD modelling (pharmacokinetic/pharmacodynamic modelling) is a technique that combines the two classical pharmacologic disciplines of pharmacokinetics and pharmacodynamics. It integrates a pharmacokinetic and a pharmacodynamic model component into one set of mathematical expressions that allows the description of the time course of effect intensity in response to administration of a drug dose. In a simple PK/PD model, K1A and K2A are the transport constants respective out of and into the hepatic arteries 302 and associated capillaries. K1V and K2V are the constants for the portal vein 304. K3 and K4 are the constants for the cells which take up contrast and K5 and K6 are the constants for the transport into and back from the bile ducts. A PK/PD model also determines as parameters one or more of the fractional volumes of each voxel that is occupied by the various compartments: arterial blood, portal venous blood, venous blood, extracellular fluid, extracellular matrix, and cells of various types, for example hepatocytes and non-hepatocytes.

In typical MR imaging, the images acquired are of high enough quality that a radiologist can look at them comfortably and reliably read them to reach his/her diagnosis. This commonly means that tens of seconds or even minutes of scan time is required to create a single image.

Techniques are being developed to speed up the creation of viewing acceptable MRI images. These techniques include, for example, parallel imaging, compressed sensing, sparse imaging, and many other techniques. Images created using these techniques may be used in various non-limiting embodiments or aspects of the present disclosure, for example, to determine the one or more characteristics of the voxel of the tissue of the patient as described herein.

Referring again to FIG. 7, in some non-limiting embodiments or aspects, at step 704, faster but noisier images may be created using an acquisition time of only a few seconds or tens of seconds. Thus, the data captured for each voxel (e.g., the measurement information, a parameter of the voxel of tissue measured at two or more time points, etc.) can better measure or approximate the shape of curve S of FIG. 1, albeit with some noise in the measurement that may still be objectionable or confusing to a human visual observer.

In some non-limiting embodiments or aspects, at step 706 of FIG. 7, the time sequence of noisier images (e.g., the measurement information, a parameter of the voxel of tissue measured at two or more time points, etc.) can be fed to a prediction model (e.g., an artificial neural network, a prediction model as described herein, etc.), the prediction model having been trained by means of supervised learning to predict, on the basis of the measurement information including a parameter of the voxel of tissue measured at two or more time points, the one or more characteristics (and/or the one or more images including or showing the one or more characteristics) at a time point and/or a time period corresponding to a time point of the two or more time points and/or at time point and/or a time period after the two or more time points (e.g., subsequent to the two or more time points, etc.).

In some non-limiting embodiments or aspects, at step 706 of FIG. 7, the time sequence of noisier images may be used to fit various model parameters to the data (e.g., to the parameter of the voxel of the tissue measured at the two or more time points, etc.). In some non-limiting embodiments or aspects, the PK/PD model of FIG. 8 may be fit to the parameter of the voxel of the tissue measured at the two or more time points (e.g., to the curve measured for each voxel, etc.). For example, image analysis and computation system 614 may fit a PK/PD model of the voxel of the tissue to the parameter of the voxel of the tissue measured at the two or more time points, and determine, based on the PK/PD model fitted to the parameter of the voxel of the tissue measured at the two or more time points, the one or more characteristics of the voxel of the tissue. As an example, the parameter(s) or necessary input functions may be measured using voxels that are fully hepatic artery and portal vein. There are many curve fitting methods known in the literature. Least squares curve fitting is a simple, but not necessarily the most efficient or effective method. One that may be advantageous to use in non-limiting embodiments or aspects of the present disclosure employs a comparison, matching, or fingerprinting to find the best fit in a set of ideal PK/PD curves precomputed for each of a discrete set of parameters and placed in a database or dictionary, as was discussed by Dr. Nicole Seiberlich during the RSNA 2018, course RC629C for a simple extracellular contrast (meaning K3-K6 are zero) as a way to measure liver perfusion. Once the PK/PD parameters for each voxel are found through the dictionary look-up, the image at a corresponding time and any future point in time may be estimated by carrying the PK/PD equations forward for each voxel and translating the concentration into a signal intensity, and PK/PD measures over time, such as drug uptake, distribution, and excretion, which allow certain conclusions on cellular function of, for example, kidneys, the liver, and the blood-brain-barrier, can be determined from the relative or absolute contrast induced tissue enhancement over time. For example, image analysis and computation system 614 may fit a PK/PD curve of a plurality of PK/PD curves precomputed for the parameter to the parameter of the voxel of the tissue measured at the two or more time points, and determine, based on the PK/PD curve fitted to the parameter at the two or more time points, the one or more characteristics of the voxel of the tissue.

In PK/PD analysis, an input function is commonly used. For example, an input function can be measured in an image, for example in an image of the aorta adjacent to the liver. It is commonly thought that a relatively narrow input function is preferred, which uses a rapid, short infusion or bolus, of a few seconds in length, of contrast followed by sufficient saline to move the bolus through the arm to the central circulation as described in U.S. patent application Ser. No. 16/346,219, the entire contents of which is incorporated herein by reference. A drawback to this short contrast bolus is that the contrast bolus broadens as it moves through the patient's central circulation, broadening to a bolus of 10 to 15 seconds in width. An additional drawback is that the bolus shape depends primarily upon the patient. Alternatively, a longer bolus, optionally >15 seconds, may be used, as described in U.S. Pat. No. 9,867,589, the entire contents of which is incorporated herein by reference. The longer bolus causes the input function to be less variably based on the patient and more determined by the injection duration. This may be preferable in some types of analysis, modelling or curve fitting described herein by limiting the range of parameters that can be expected to occur in the model. One drawback to the longer bolus may be that the normal arterial, portal venous, or other phase images are not available because of the overlap in time. If it is desirable to present the "standard" images to the radiologist, image analysis and computation system 614 may analyse the one or more characteristics of the model for each voxel and the "standard images" may be constructed from the models parameters for that voxel. This longer bolus approach may be especially beneficial in PET imaging to avoid detector saturation or pulse pile up and dead space correction effects. It may also be beneficial to CT by enabling fewer scans to be taken because the contrast levels are changing at a slower rate and the timing can be better predicted and not as variable depending upon the patient's physiology. Where appropriate to a diagnostic question being asked and the characteristics being assessed, simplified PK/PD models such as Patlak analysis and/or other such models be used.

In another non-limiting embodiment or aspect, curve S is approximated by, or curve S is decomposed into, a set of selected basis functions (e.g., a set of polynomial function, a set of Laplace functions, a set of Fourier functions, etc.). For example, a basis function is an element of a particular basis for a function space. Every continuous function in the function space can be represented as a linear combination of basis functions, just as every vector in a vector space can be represented as a linear combination of basis vectors. As an example, image analysis and computation system 614 may approximate a curve representing one or more characteristics of a voxel of tissue with a set of basis functions, fit the approximated curve to one or more parameters of the voxel of the tissue measured at two or more time points, and determine, based on the approximated curve fitted to the parameter of the voxel of the tissue measured at the two or more time points, the one or more characteristics of the voxel of the tissue. In such an example, first pass contrast enhancement over time curve may be modelled as a gamma variate curve according to the following Equation (1):

$$C(t)=K(t-AT)^a \cdot *\exp(-(t-AT)/b \quad (1)$$

where t=time after injection, C(t)=concentration at time, K=constant scale factor, AT=appearance time, and a, b=arbitrary parameters for t>AT.

The curve S may be approximated by two or more gamma variate curves to represent the first pass part of the A curve, the first pass part of the V curve, with optionally a third gamma variate curve to represent the steady state recirculation and redistribution, and one linearly increasing curve C(t)=m(t−AT')+n where m & n are arbitrary parameters, AT' is start of the linear rise, and t is time after injection for t>AT'. However non-limiting embodiments or aspects are not limited to using gamma variate curves for the modeling, and any other set of basis functions (e.g., a set of polynomial function, a set of Laplace functions, a set of Fourier functions, etc.) may be used for the modeling, and any computationally efficient curve fitting program may be used determine the best fit parameters to a measured curve S. Once the basis function parameters for each voxel are found through the curve fitting process, the image at a corresponding time and any point in time may be estimated by carrying the equations forward or backward for each voxel and translating the concentration into a signal intensity for the time t desired. For example, image analysis and computation system 614 may fit a curve of a plurality of curves precomputed for one or more parameters with a set of basis functions to one or more parameters of a voxel of tissue measured at two or more time points, and determine, based on the curve fitted to the parameter of the voxel of the tissue measured at the two or more time points, one or more characteristics of the voxel of the tissue.

As described elsewhere herein, a longer contrast bolus or injection may cause a curve S to have a slower rise and fall, which may affect or constrain the basis function parameters that are expected in the model, and so may simplify, speed up, or increase the accuracy of the curve fitting activity and/or the resulting model.

Once a model or algorithm, for example a PK/PD, basis function, AI or other model known to those skilled in the art, is fit to the two or more time points for each voxel, images may be created or information derived that could never be independently measured in the physical situation. The "white liver" of FIG. 9 is a non-limiting example of this. Another non-limiting example or aspect is an image or sequence of images created to show the contrast flowing through the liver over time as if contrast only came into the liver through the portal vein and none came in through the portal artery, or vice-versa. Similarly, images may be created that would have occurred with the use of a very fast or short bolus, even though a longer bolus would have been actually used in the overall imaging protocol. This ability to create images that were physically impossible to measure given the actual imaging protocol used can lead to new understandings in the diagnosis, nuances or conditions, or treatments and response to treatment of disease. This is in addition to the images that are currently done of the PK/PD parameters themselves, for example blood volume pass or the various K or composite constant maps.

Still referring to FIG. 7, in some non-limiting embodiments or aspects, at step 708, image analysis and computation system 614 may analyse the one or more characteristics associated with the voxel of the tissue of the patient and/or the one or more images the one or more characteristics associated with the tissue of the patient to calculate absolute values for the wash-out of a lesion over time, compared to the arterial phase enhancement (e.g., liver). Currently the washout of a lesion is usually assessed visually, by comparing the enhancement of the surrounding tissue with that of the lesion during contrast phases that follow the arterial phase. This however bares the risk of misinterpretation because some contrast agents (such as the liver specific agent Primovist®) may be taken up by the liver cells that surround or are part of the lesion (e.g., potentially metastases or other tumors). This beginning uptake of Primovist® may then create the illusion of a stronger contrast between lesion and the surrounding tissue and can be misinterpreted as washout when there is actually none. This bares the risk of misdiagnosis without the analysis of non-limiting embodiments or aspects of the present disclosure to enable the separate or discrete decomposition and/or visualization of these aspects.

In some non-limiting embodiments or aspects, an examination region includes the liver or a portion of the liver of a mammal (preferably a human). In some non-limiting embodiments or aspects, an examination region may include the lungs or a portion thereof. The lungs receive circulation of deoxygenated blood from the right heart and also oxygenated blood from the left heart. In addition, the lungs receive gas through the airways. Thus, the lungs may receive contrast either intravenously or gaseous contrast through the airways. Accordingly, non-limiting embodiments or aspects of the present disclosure may apply to inhaled contrast, as well as IV injected contrast. In addition, most tissue acts as a lymphatic system (e.g., the glymphatic system in the brain) for circulation of fluids through the extracellular space of tissue. Non-limiting embodiments or aspects of the present disclosure may include contrast flows, or lack thereof, through this lymphatic or glymphatic system.

In various non-limiting embodiments or aspects described herein, various tissue characteristics and voxel parameters have been listed for understanding and disclosure. It should be recognized that these are exemplary and not limiting or an exhaustive list. Other characteristics and/or parameters known in the medical art may be used. In addition, characteristics and/or parameters in research or yet to be discovered may also benefit from the application of non-limiting embodiments or aspects of the present disclosure in the processing, imaging, and/or analysing of the data from an imaging study and/or a sequence of studies.

What is claimed is:

1. A computer-implemented method comprising:
    obtaining measurement information associated with a parameter of a voxel of an image of tissue of a patient, wherein the measurement information is measured at two or more time points to provide first measurement information associated with the parameter of the voxel at a first time point of the two or more time points and second measurement information associated with the parameter of the voxel at a second time point of the two or more time points, wherein the two or more time points occur before one or more tissue characteristics are separable or discernible in another image generated based on the parameter of the voxel measured at a time point, and wherein the one or more tissue characteristics comprise:
        a concentration of contrast agent in arteries;
        a concentration of contrast agent in veins;
        a concentration of contrast agent in cells;
        a summed enhancement of a concentration of contrast agent in arteries, veins, and cells;
        one or more pharmacokinetic parameters associated with contrast agent movement through tissue spaces; or
        any combination thereof; and
    determining one or more characteristics of the voxel of the image of tissue based on the first measurement information associated with the parameter of the voxel at the first time point, the second measurement information associated with the parameter of the voxel at the second time point, and a desired rate and/or plateau level of a concentration of a contrast agent delivered to the patient.

2. The computer-implemented method of claim 1, wherein the one or more characteristics of the voxel of the image of tissue are further determined based on at least one of the following: a height of the patient, a weight of the patient, an age of the patient, a gender of the patient, a heart rate of the patient, a cardiac output of the patient, a clinical symptom of the patient, a bilirubin level of the patient, or any combination thereof.

3. The computer-implemented method of claim 1, wherein the one or more characteristics of the voxel of the image of tissue are determined for a time point corresponding to at least one of the two or more time points.

4. The computer-implemented method of claim 1, wherein the one or more characteristics of the voxel of the image of tissue are determined for a time point subsequent to the two or more time points, and the method further comprising:
    generating, based on the one or more tissue characteristics, one or more images including the one or more characteristics of the voxel of the image of tissue at the time point after the two or more time points.

5. The computer-implemented method of claim 1, wherein the one or more characteristics of the voxel of the image of tissue are determined for a time point subsequent to the two or more time points, and further comprising:

determining that the measurement information associated with the parameter of the voxel of the image of tissue of the patient includes a threshold amount of measurement information associated with determining the one or more characteristics of the voxel of the image of tissue; and in response to determining that the measurement information includes the threshold amount of measurement information, controlling an imaging system to automatically stop acquisition of the measurement information.

6. The computer-implemented method of claim 1, wherein the one or more characteristics of the voxel of the image of tissue are determined for a time point subsequent to the two or more time points, and wherein determining the one or more characteristics of the voxel of the image of tissue includes:

feeding the measurement information associated with the parameter of the voxel of the image of tissue of the patient to a prediction model, the prediction model having been trained by means of supervised learning to predict, on the basis of the measurement information associated with the parameter at the two or more time points, the one or more characteristics of the voxel of the image of tissue.

7. The computer-implemented method of claim 1, wherein the one or more characteristics of the voxel of the image of tissue are determined for a time point subsequent to the two or more time points, and wherein determining the one or more characteristics of the voxel of the image of tissue includes:

fitting a pharmacokinetic/pharmacodynamic (PK/PD) model of the voxel of the image of tissue to the parameter of the voxel of the image of tissue measured at the two or more time points; and determining, based on the PK/PD model fitted to the parameter of the voxel of the image of tissue measured at the two or more time points, the one or more characteristics of the voxel of the image of tissue.

8. The computer-implemented method of claim 1, wherein the one or more characteristics of the voxel of the image of tissue are determined for a time point subsequent to the two or more time points, and wherein determining the one or more characteristics of the voxel of the image of tissue includes:

fitting a PK/PD curve of a plurality of PK/PD curves precomputed for the parameter to the parameter of the voxel of the image of tissue measured at the two or more time points; and determining, based on the PK/PD curve fitted to the parameter at the two or more time points, the one or more characteristics of the voxel of the image of tissue.

9. The computer-implemented method of claim 1, wherein the one or more characteristics of the voxel of the image of tissue are determined for a time point subsequent to the two or more time points, and wherein determining the one or more characteristics of the voxel of the image of tissue includes:

approximating a curve representing the one or more characteristics of the voxel of the image of tissue with a set of basis functions;

fitting the approximated curve to the parameter of the voxel of the image of tissue measured at the two or more time points; and determining, based on the approximated curve fitted to the parameter of the voxel of the image of tissue measured at the two or more time points, the one or more characteristics of the voxel of the image of tissue.

10. The computer-implemented method of claim 1, wherein the one or more characteristics of the voxel of the image of tissue are determined for a time point subsequent to the two or more time points, and wherein determining the one or more characteristics of the voxel of the image of tissue includes:

fitting a curve of a plurality of curves precomputed for the parameter with a set of basis functions to the parameter of the voxel of the image of tissue measured at the two or more time points; and determining, based on the curve fitted to the parameter of the voxel of the image of tissue measured at the two or more time points, the one or more characteristics of the voxel of the image of tissue.

11. A system comprising:

one or more processors programmed and/or configured to:

obtain measurement information associated with a parameter of a voxel of an image of tissue of a patient, wherein the measurement information is measured at two or more time points to provide first measurement information associated with the parameter of the voxel at a first time point of the two or more time points and second measurement information associated with the parameter of the voxel at a second time point of the two or more time points, wherein the two or more time points occur before one or more tissue characteristics are separable or discernible in another image generated based on the parameter of the voxel measured at a time point, and wherein the one or more tissue characteristics comprise:

a concentration of contrast agent in arteries;
a concentration of contrast agent in veins;
a concentration of contrast agent in cells;
a summed enhancement of a concentration of contrast agent in arteries, veins, and cells;
one or more pharmacokinetic parameters associated with contrast agent movement through tissue spaces; or
any combination thereof; and determine one or more characteristics of the voxel of the image of tissue based on the first measurement information associated with the parameter of the voxel at the first time point, the second measurement information associated with the parameter of the voxel at the second time point, and a desired rate and/or plateau level of a concentration of a contrast agent delivered to the patient.

12. The system of claim 11, wherein the one or more characteristics of the voxel of the image of tissue are determined for a time point subsequent to the two or more time points and wherein the one or more processors are further programmed and/or configured to:

generate, based on the one or more tissue characteristics, one or more images including the one or more characteristics of the voxel of the image of tissue at the time point after the two or more time points.

13. The system of claim 11, wherein the one or more characteristics of the voxel of the image of tissue are determined for a time point subsequent to the two or more time points and wherein the one or more processors are further programmed and/or configured to:

determine that the measurement information associated with the parameter of the voxel of the image of tissue of the patient includes a threshold amount of measurement information associated with determining the one or more characteristics of the voxel of the image of tissue; and in response to determining that the measurement information includes the threshold amount of measurement information, control an imaging system to automatically stop acquisition of the measurement information.

14. The system of claim 11, wherein the one or more characteristics of the voxel of the image of tissue are determined for a time point subsequent to the two or more time points and wherein the one or more processors are further programmed and/or configured to determine the one or more characteristics of the voxel of the image of tissue by:

feeding the measurement information associated with the parameter of the voxel of the image of tissue of the patient to a prediction model, the prediction model having been trained by means of supervised learning to predict, on the basis of the measurement information associated with the parameter at the two or more time points, the one or more characteristics of the voxel of the image of tissue.

15. The system of claim 11, wherein the one or more characteristics of the voxel of the image of tissue are determined for a time point subsequent to the two or more time points and wherein the one or more processors are further programmed and/or configured to determine the one or more characteristics of the voxel of the image of tissue by:

fitting a pharmacokinetic/pharmacodynamic (PK/PD) model of the voxel of the image of tissue to the parameter of the voxel of the image of tissue measured at the two or more time points; and determining, based on the PK/PD model fitted to the parameter of the voxel of the image of tissue measured at the two or more time points, the one or more characteristics of the voxel of the image of tissue.

16. The system of claim 11, wherein the one or more characteristics of the voxel of the image of tissue are determined for a time point subsequent to the two or more time points and wherein the one or more processors are further programmed and/or configured to determine the one or more characteristics of the voxel of the image of tissue by:

approximating a curve representing the one or more characteristics of the voxel of the image of tissue with a set of basis functions;

fitting the approximated curve to the parameter of the voxel of the image of tissue measured at the two or more time points; and determining, based on the approximated curve fitted to the parameter of the voxel of the image of tissue measured at the two or more time points, the one or more characteristics of the voxel of the image of tissue.

17. A computer program product comprising at least one non-transitory computer-readable medium including program instructions that, when executed by at least one processor, cause the at least one processor to:

obtain measurement information associated with a parameter of a voxel of an image of tissue of a patient, wherein the measurement information is measured at two or more time points to provide first measurement information associated with the parameter of the voxel at a first time point of the two or more time points and second measurement information associated with the parameter of the voxel at a second time point of the two or more time points, wherein the two or more time points occur before one or more tissue characteristics are separable or discernible in another image generated based on the parameter of the voxel measured at a time point, and wherein the one or more tissue characteristics comprise:

a concentration of contrast agent in arteries;
a concentration of contrast agent in veins;
a concentration of contrast agent in cells;
a summed enhancement of a concentration of contrast agent in arteries, veins, and cells;
one or more pharmacokinetic parameters associated with contrast agent movement through tissue spaces; or
any combination thereof; and determine one or more characteristics of the voxel of the image of tissue based on the first measurement information associated with the parameter of the voxel at the first time point, the second measurement information associated with the parameter of the voxel at the second time point, and a desired rate and/or plateau level of a concentration of a contrast agent delivered to the patient.

18. The computer program product of claim 17, wherein the one or more characteristics of the voxel of the image of tissue are determined for a time point subsequent to the two or more time points, and wherein the instructions further cause the at least one processor to:

generate, based on the one or more tissue characteristics, one or more images including the one or more characteristics of the voxel of the image of tissue at the time point after the two or more time points.

19. The computer program product of claim 17, wherein the one or more characteristics of the voxel of the image of tissue are determined for a time point subsequent to the two or more time points, and wherein the instructions further cause the at least one processor to:

determine that the measurement information associated with the parameter of the voxel of the image of tissue of the patient includes a threshold amount of measurement information associated with determining the one or more characteristics of the voxel of the image of tissue; and in response to determining that the measurement information includes the threshold amount of measurement information, control an imaging system to automatically stop acquisition of the measurement information.

20. The computer program product of claim 17, wherein the one or more characteristics of the voxel of the image of tissue are determined for a time point subsequent to the two or more time points, and wherein the instructions cause the at least one processor to determine the one or more characteristics of the voxel of the image of tissue by:

feeding the measurement information associated with the parameter of the voxel of the image of tissue of the patient to a prediction model, the prediction model having been trained by means of supervised learning to predict, on the basis of the measurement information associated with the parameter at the two or more time points, the one or more characteristics of the voxel of the image of tissue.

21. The computer program product of claim 17, wherein the one or more characteristics of the voxel of the image of tissue are determined for a time point subsequent to the two or more time points, and wherein the instructions cause the at least one processor to determine the one or more characteristics of the voxel of the image of tissue by:

fitting a pharmacokinetic/pharmacodynamic (PK/PD) model of the voxel of the image of tissue to the parameter of the voxel of the image of tissue measured at the two or more time points; and determining, based on the PK/PD model fitted to the parameter of the voxel of the image of tissue measured at the two or more time points, the one or more characteristics of the voxel of the image of tissue.

22. The computer program product of claim 17, wherein the one or more characteristics of the voxel of the image of tissue are determined for a time point subsequent to the two or more time points, and wherein the instructions cause the at least one processor to determine the one or more characteristics of the voxel of the image of tissue by:

approximating a curve representing the one or more characteristics of the voxel of the image of tissue with a set of basis functions;

fitting the approximated curve to the parameter of the voxel of the image of tissue measured at the two or more time points; and determining, based on the approximated curve fitted to the parameter of the voxel of the image of tissue measured at the two or more time points, the one or more characteristics of the voxel of the image of tissue.

23. The computer-implemented method of claim 1, wherein the contrast agent is delivered to the patient in a double injection protocol including a first injection of the contrast agent in which the contrast agent equilibrates in the body and is taken up by the target tissues and a second injection of the contrast agent after the first injection, wherein the measurement information includes one or more images taken after the first injection and before the second injection after the contrast agent equilibrates in the body and one or more additional images taken after the second injection that are timed to enable visualization and/or measurement of blood vessel enhancement, and wherein the one or more characteristics of the voxel of the image of tissue are determined by subtracting the one or more images from the one or more additional images to derive images which show blood vessel enhancement separate from equilibrium uptake at the corresponding points in time.

* * * * *

UNITED STATES PATENT AND TRADEMARK OFFICE
CERTIFICATE OF CORRECTION

PATENT NO. : 11,915,361 B2
APPLICATION NO. : 17/753564
DATED : February 27, 2024
INVENTOR(S) : Rohrer et al.

It is certified that error appears in the above-identified patent and that said Letters Patent is hereby corrected as shown below:

In the Drawings

In Fig. 7, Sheet 6 of 10, for Tag "720", in Line 1, delete "Inupt" and insert -- Input --, therefor.
In Fig. 9, Sheet 8 of 10, delete "Hepatocyted and vessels white," and insert -- Hepatocytes and white vessels, --, therefor.

In the Specification

In Column 2, Line 48, delete "diethylenetriaminepentaacetic" and insert -- diethylenetriamine pentaacetic --, therefor.
In Column 2, Line 51, delete "radical (EOB)" and insert -- (EOB) radical --, therefor.
In Column 11, Line 60, delete "one the" and insert -- one of the --, therefor.
In Column 12, Lines 35-36, delete "plurality of plurality of" and insert -- plurality of --, therefor.
In Column 12, Line 52, delete "clause 1-10," and insert -- clauses 1-10, --, therefor.
In Column 13, Line 11, delete "one the" and insert -- one of the --, therefor.
In Column 13, Line 56, delete "plurality of plurality of" and insert -- plurality of --, therefor.
In Column 14, Line 36, delete "one the" and insert -- one of the --, therefor.
In Column 15, Line 14, delete "plurality of plurality of" and insert -- plurality of --, therefor.
In Column 16, Line 10, delete "Tlw" and insert -- T1w --, therefor.
In Column 18, Line 58, delete "4(d)," and insert -- 4(d). --, therefor.
In Column 20, Line 23, delete "(PET/MRI)" and insert -- imaging (PET/MRI) --, therefor.
In Column 23, Line 4-5, delete "diffusion weighted (DWI)," and insert -- diffusion weighted imaging (DWI), --, therefor.
In Column 24, Line 6, delete "(over" and insert -- over --, therefor.
In Column 25, Line 44, delete "(e.g.," and insert -- e.g., --, therefor.
In Column 26, Line 51, delete "one more" and insert -- one or more --, therefor.
In Column 26, Line 55, delete "one more" and insert -- one or more --, therefor.
In Column 26, Line 57, delete "characteristics," and insert -- characteristics), --, therefor.
In Column 30, Line 34, delete "$C(t)=K(t-AT)a.* \exp(-(t-AT)/b$" and insert -- $C(t)=K(t-AT)a.* \exp(-(t-AT)/b)$ --, therefor.

Signed and Sealed this
Twenty-third Day of April, 2024

Katherine Kelly Vidal
*Director of the United States Patent and Trademark Office*

CERTIFICATE OF CORRECTION (continued)
U.S. Pat. No. 11,915,361 B2

In Column 31, Line 36, delete "bares" and insert -- bears --, therefor.
In Column 31, Line 43, delete "bares" and insert -- bears --, therefor.